United States Patent
Ikeuchi

(10) Patent No.: US 10,280,212 B2
(45) Date of Patent: *May 7, 2019

(54) COMPOSITE COMPRISING ANTIBODY CAPABLE OF BINDING TO INTRANUCLEAR PROTEIN OF INFLUENZA VIRUS

(71) Applicant: PANASONIC INTELLECTUAL PROPERTY MANAGEMENT CO., LTD., Osaka (JP)

(72) Inventor: Emina Ikeuchi, Tokyo (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/970,597

(22) Filed: May 3, 2018

(65) Prior Publication Data

US 2018/0251529 A1    Sep. 6, 2018

Related U.S. Application Data

(63) Continuation of application No. 15/648,287, filed on Jul. 12, 2017, now Pat. No. 9,988,435, which is a continuation-in-part of application No. 15/296,180, filed on Oct. 18, 2016, now abandoned.

(60) Provisional application No. 62/344,152, filed on Jun. 1, 2016.

(51) Int. Cl.
```
C12N 15/70      (2006.01)
C07K 16/10      (2006.01)
A61K 47/68      (2017.01)
G01N 33/569     (2006.01)
```

(52) U.S. Cl.
CPC ...... *C07K 16/1018* (2013.01); *A61K 47/6839* (2017.08); *C12N 15/70* (2013.01); *G01N 33/56983* (2013.01); *C07K 2317/22* (2013.01); *C07K 2317/33* (2013.01); *C07K 2317/565* (2013.01); *C07K 2317/569* (2013.01); *C07K 2317/92* (2013.01); *G01N 2333/11* (2013.01)

(58) Field of Classification Search
None
See application file for complete search history.

(56) References Cited

U.S. PATENT DOCUMENTS

2014/0302063 A1    10/2014    Hufton

FOREIGN PATENT DOCUMENTS

CN    103804493 A    5/2014
WO    94/09136 A1    4/1994

OTHER PUBLICATIONS

Non-Final Office Action issued in U.S. Appl. No. 15/296,180, dated Dec. 14, 2017.
Final Office Action issued in U.S. Appl. No. 15/296,180, dated Mar. 16, 2017.
Non-Final Office Action issued in U.S. Appl. No. 15/648,287, dated Dec. 14, 2017.
Notice of Allowance issued in U.S. Appl. No. 15/648,287, dated Feb. 6, 2018.
Simon E. Hufton et. al., "The Breadth of Cross Sub-Type Neutralisation Activity of a Single Domain Antibody to Influenza Hemagglutinin Can Be Increased by Antibody Valency," PLOS ONE [www.plosone.org], Aug. 2014, vol. 9, Issue 8, e103294, pp. 1-19.
Rivera et al., Serologic survey of viral antibodies in the Peruvian alpaca (*Lama pacos*), 1987, American Journal of Veterinary Research, vol. 48, No. 2, pp. 189-191 (abstract provided).
Vajdos et al. Comprehensive Functional Maps of the Antigenbinding Site of an Anti-ErbB2 Antibody Obtained with Shotgun Scanning Mutagenesis, 2002, Journal of Molecular Biology, vol. 320, pp. 415-428.
Non-Final Office Action issued in U.S. Appl. No. 15/296,180, dated Dec. 7, 2016.
Hanke, L. et al. "The Antiviral Mechanism of an Influenza A Virus Nucleoprotein-Specific Single-Domain Antibody Fragment," American Society for Microbiology, vol. 7, Issue 6, Nov./Dec. 2016; pp. 1-11; downloaded from mbio.asm.org on Dec. 11, 2017—Published by mbio.asm.org.

*Primary Examiner* — Benjamin P Blumel
(74) *Attorney, Agent, or Firm* — McDermott Will & Emery LLP

(57) ABSTRACT

The present invention provides a composite comprising a novel antibody and at least one selected from the group consisting of a solid phase support and a labeled substance. The antibody consists of the amino acid sequence represented by SEQ ID NO: 08, and is capable of binding to an intranuclear protein of an influenza virus type A. The influenza virus type A is at least one selected from the group consisting of H1N1, H2N2, H3N2, and H7N9. The antibody is bound to the at least one selected from the group consisting of the solid phase support and the labeled substance. The present invention also provides a detection device and a detection method using the composite.

4 Claims, 17 Drawing Sheets
Specification includes a Sequence Listing.

SEQUENCE LISTING

```
<160> NUMBER OF SEQ ID NOS: 25

<210> SEQ ID NO 1
<211> LENGTH: 10
<212> TYPE: PRT
<213> ORGANISM: Lama pacos

<400> SEQUENCE: 1

Gly Arg Thr Phe Ile Asn Leu Asp Met Gly
1               5                   10

<210> SEQ ID NO 2
<211> LENGTH: 17
<212> TYPE: PRT
<213> ORGANISM: Lama pacos

<400> SEQUENCE: 2

Ala Ile Thr Arg Asn Gly Ala Ile Thr Ser Tyr Ala Asp Ser Ala Lys
1               5                   10                  15

Gly

<210> SEQ ID NO 3
<211> LENGTH: 15
<212> TYPE: PRT
<213> ORGANISM: Lama pacos

<400> SEQUENCE: 3

Tyr Ser Ile Ser Asn Tyr Gly Ser Gly Trp Tyr Lys Pro Asp Tyr
1               5                   10                  15

<210> SEQ ID NO 4
<211> LENGTH: 25
<212> TYPE: PRT
<213> ORGANISM: Lama pacos

<400> SEQUENCE: 4

Glu Val Gln Leu Val Glu Ser Gly Gly Leu Val Gln Ala Gly Asp
1               5                   10                  15

Ser Leu Arg Leu Ser Cys Ala Ala Ser
            20                  25

<210> SEQ ID NO 5
<211> LENGTH: 14
<212> TYPE: PRT
```

<213> ORGANISM: Lama pacos

<400> SEQUENCE: 5

```
Trp Phe Arg Gln Pro Pro Gly Lys Glu Arg Glu Tyr Val Ala
 1               5                  10
```

<210> SEQ ID NO 6
<211> LENGTH: 32
<212> TYPE: PRT
<213> ORGANISM: Lama pacos

<400> SEQUENCE: 6

```
Arg Phe Thr Ile Ser Arg Asp Asn Ala Lys Asn Thr Val Ser Leu Glu
 1               5                  10                  15

Met Asn Ser Leu Lys Pro Glu Asp Thr Gly Val Tyr Tyr Cys Ala Ala
                20                  25                  30
```

<210> SEQ ID NO 7
<211> LENGTH: 11
<212> TYPE: PRT
<213> ORGANISM: Lama pacos

<400> SEQUENCE: 7

```
Trp Gly Gln Gly Ala Gln Val Thr Val Ser Ser
 1               5                  10
```

<210> SEQ ID NO 8
<211> LENGTH: 124
<212> TYPE: PRT
<213> ORGANISM: Lama pacos

<400> SEQUENCE: 8

```
Glu Val Gln Leu Val Glu Ser Gly Gly Leu Val Gln Ala Gly Asp
 1               5                  10                  15

Ser Leu Arg Leu Ser Cys Ala Ala Ser Gly Arg Thr Phe Ile Asn Leu
                20                  25                  30

Asp Met Gly Trp Phe Arg Gln Pro Pro Gly Lys Glu Arg Glu Tyr Val
            35                  40                  45

Ala Ala Ile Thr Arg Asn Gly Ala Ile Thr Ser Tyr Ala Asp Ser Ala
        50                  55                  60

Lys Gly Arg Phe Thr Ile Ser Arg Asp Asn Ala Lys Asn Thr Val Ser
 65                  70                  75                  80

Leu Glu Met Asn Ser Leu Lys Pro Glu Asp Thr Gly Val Tyr Tyr Cys
                 85                  90                  95

Ala Ala Tyr Ser Ile Ser Asn Tyr Gly Ser Gly Trp Tyr Lys Pro Asp
                100                 105                 110

Tyr Trp Gly Gln Gly Ala Gln Val Thr Val Ser Ser
            115                 120
```

<210> SEQ ID NO 9
<211> LENGTH: 15
<212> TYPE: DNA
<213> ORGANISM: Artificial Sequence
<220> FEATURE:
<223> OTHER INFORMATION: Synthesized Primer

<400> SEQUENCE: 9
ggtggtcctg gctgc                                                    15

<210> SEQ ID NO 10
<211> LENGTH: 50

```
<212> TYPE: DNA
<213> ORGANISM: Artificial Sequence
<220> FEATURE:
<223> OTHER INFORMATION: Synthesized Primer

<400> SEQUENCE: 10
ctgctcctcg cggcccagcc ggccatggct sagktgcagc tcgtggagtc          50

<210> SEQ ID NO 11
<211> LENGTH: 21
<212> TYPE: DNA
<213> ORGANISM: Artificial Sequence
<220> FEATURE:
<223> OTHER INFORMATION: Synthesized Primer

<400> SEQUENCE: 11
tggggtcttc gctgtggtgc g                                          21

<210> SEQ ID NO 12
<211> LENGTH: 21
<212> TYPE: DNA
<213> ORGANISM: Artificial Sequence
<220> FEATURE:
<223> OTHER INFORMATION: Synthesized Primer

<400> SEQUENCE: 12
ttgtggtttt ggtgtcttgg g                                          21

<210> SEQ ID NO 13
<211> LENGTH: 45
<212> TYPE: DNA
<213> ORGANISM: Artificial Sequence
<220> FEATURE:
<223> OTHER INFORMATION: Synthesized Primer

<400> SEQUENCE: 13
tttgctctgc ggccgcagag gccgtggggt cttcgctgtg gtgcg                45

<210> SEQ ID NO 14
<211> LENGTH: 46
<212> TYPE: DNA
<213> ORGANISM: Artificial Sequence
<220> FEATURE:
<223> OTHER INFORMATION: Synthesized Primer

<400> SEQUENCE: 14
tttgctctgc ggccgcagag gccgattgtg gttttggtgt cttggg               46

<210> SEQ ID NO 15
<211> LENGTH: 13
<212> TYPE: DNA
<213> ORGANISM: Artificial Sequence
<220> FEATURE:
<223> OTHER INFORMATION: Synthesized DNA which represents SfiI(a) site

<400> SEQUENCE: 15
ggcccagccg gcc                                                   13

<210> SEQ ID NO 16
<211> LENGTH: 13
<212> TYPE: DNA
<213> ORGANISM: Artificial Sequence
<220> FEATURE:
<223> OTHER INFORMATION: Synthesized DNA which represents SfiI(b) site

<400> SEQUENCE: 16
```
ggcctctgcg gcc 13

<210> SEQ ID NO 17
<211> LENGTH: 4057
<212> TYPE: DNA
<213> ORGANISM: Artificial Sequence
<220> FEATURE:
<223> OTHER INFORMATION: Synthesized plamid Vector 1

<400> SEQUENCE: 17

| | |
|---|---|
| gacgaaaggg cctcgtgata cgcctatttt tataggttaa tgtcatgata ataatggttt | 60 |
| cttagacgtc aggtggcact tttcggggaa atgtgcgcgg aaccccttatt tgtttatttt | 120 |
| tctaaataca ttcaaatatg tatccgctca tgagacaata accctgataa atgcttcaat | 180 |
| aatattgaaa aaggaagagt atgagtattc aacatttccg tgtcgccctt attccctttt | 240 |
| ttgcggcatt ttgccttcct gttttttgctc acccagaaac gctggtgaaa gtaaaagatg | 300 |
| ctgaagatca gttgggtgca cgagtgggtt acatcgaact ggatctcaac agcggtaaga | 360 |
| tccttgagag ttttcgcccc gaagaacgtt ttccaatgat gagcactttt aaagttctgc | 420 |
| tatgtggcgc ggtattatcc cgtattgacg ccgggcaaga gcaactcggt cgccgcatac | 480 |
| actattctca gaatgacttg gttgagtact caccagtcac agaaaagcat cttacgdatg | 540 |
| gcatgacagt aagagaatta tgcagtgctg ccataaccat gagtgataac actgcggcca | 600 |
| acttacttct gacaacgatc ggaggaccga aggagctaac cgcttttttg cacaacatgg | 660 |
| gggatcatgt aactcgcctt gatcgttggg aaccggagct gaatgaagcc ataccaaacg | 720 |
| acgagcgtga ccacacgatg cctgtagcaa tggcaacaac gttgcgcaaa ctattaactg | 780 |
| gcgaactact tactctagct tcccggcaac aattaataga ctggatggag gcggataaag | 840 |
| ttgcaggacc acttctgcgc tcggcccttc cggctggctg gtttattgct gataaatctg | 900 |
| gagccggtga gcgtgggtct cgcggtatca ttgcagcact ggggccagat ggtaagccct | 960 |
| cccgtatcgt agttatctac acgacgggga gtcaggcaac tatggatgaa cgaaatagac | 1020 |
| agatcgctga gataggtgcc tcactgatta agcattggta actgtcagac caagtttact | 1080 |
| catatatact ttagattgat ttaaaacttc attttttaatt taaaaggatc taggtgaaga | 1140 |
| tcctttttga taatctcatg accaaaatcc cttaacgtga gttttcgttc cactgagcgt | 1200 |
| cagaccccgt agaaaagatc aaaggatctt cttgagatcc ttttttttctg cgcgtaatct | 1260 |
| gctgcttgca acaaaaaaa ccaccgctac cagcggtggt ttgtttgccg gatcaagagc | 1320 |
| taccaactct ttttccgaag gtaactggct tcagcagagc gcagatacca atactgtcc | 1380 |
| ttctagtgta gccgtagtta ggccaccact tcaagaactc tgtagcaccg cctacatacc | 1440 |
| tcgctctgct aatcctgtta ccagtggctg ctgccagtgg cgataagtcg tgtcttaccg | 1500 |
| ggttggactc aagacgatag ttaccggata aggcgcagcg gtcgggctga acggggggtt | 1560 |
| cgtgcacaca gcccagcttg gagcgaacga cctacaccga actgagatac ctacagcgtg | 1620 |
| agctatgaga aagcgccacg cttcccgaag ggagaaaggc ggacaggtat ccggtaagcg | 1680 |
| gcagggtcgg aacaggagag cgcacgaggg agcttccagg gggaaacgcc tggtatcttt | 1740 |
| atagtcctgt cgggtttcgc cacctctgac ttgagcgtcg attttttgtga tgctcgtcag | 1800 |
| gggggcggag cctatggaaa aacgccagca acgcggcctt tttacggttc ctggccttt | 1860 |
| gctggccttt tgctcacatg ttctttcctg cgttatcccc tgattctgtg ataaccgta | 1920 |
| ttaccgcctt tgagtgagct gataccgctc gccgcagccg aacgaccgag cgcagcgagt | 1980 |
| cagtgagcga ggaagcggaa gagcgcccaa tacgcaaacc gcctctcccc gcgcgttggc | 2040 |

```
cgattcatta atgcagctgg cacgacaggt ttcccgactg aaagcgggc agtgagcgca    2100
acgcaattaa tgtgagttag ctcactcatt aggcacccca ggctttacac tttatgcttc    2160
cggctcgtat gttgtgtgga attgtgagcg ataacaatt tcacacagga aacagctatg    2220
accatgatta cgccaagctt cgaaggagac agtcataatg aaatacctgc tgccgaccgc    2280
tgctgctggt ctgctgctcc tcgcggccca gccggccatg gagctcaaga tgacacagac    2340
tacatcctcc ctgtcagcct ctctgggaga cagagtcacc atcagttgca gggcaagtca    2400
ggacattagc gattatttaa actggtatca gcagaaacca gatggaactg ttaaactcct    2460
gatctattac acatcaagtt tacactcagg agtcccatca aggttcagtg gcggtgggtc    2520
tggaacagat tattctctca ccattagcaa cctggagcaa gaagatattg ccacttactt    2580
tgccaacag ggtaatacgc ttccgtggac gtttggtgga ggcaccaagc tggaaatcaa    2640
acgggctgat gctgcaccaa ctgtaggcct ctgcggccgc agagcaaaaa ctcatctcag    2700
aagaggatct gaatggggcc gcatagggtt ccggtgattt tgattatgaa agatggcaa    2760
acgctaataa gggggctatg accgaaaatg ccgatgaaaa cgcgctacag tctgacgcta    2820
aaggcaaact tgattctgtc gctactgatt acggtgctgc tatcgatggt ttcattggtg    2880
acgtttccgg ccttgctaat ggtaatggtg ctactggtga ttttgctggc tctaattccc    2940
aaatggctca gtcggtgac ggtgataatt cacctttaat gaataatttc cgtcaatatt    3000
taccttccct ccctcaatcg gttgaatgtc gcccttttgt ctttagcgct ggtaaaccat    3060
atgaattttc tattgattgt gacaaaataa acttattccg tggtgtcttt gcgtttcttt    3120
tatatgttgc cacctttatg tatgtatttt ctacgtttgc taacatactg cgtaataagg    3180
agtcttaata agaattcact ggccgtcgtt ttacaacgtc gtgactggga aaaccctggc    3240
gttacccaac ttaatcgcct tgcagcacat ccccctttcg ccagctggcg taatagcgaa    3300
gaggcccgca ccgatcgccc ttcccaacag ttgcgcagcc tgaatggcga atggcgcctg    3360
atgcggtatt ttctccttac gcatctgtgc ggtatttcac accgcatatg aaaattgtaa    3420
gcgttaatat tttgttaaaa ttcgcgttaa attttttgtta atcagctca ttttttaacc    3480
aataggccga atcggcaaa atcccttata atcaaaaga atagaccgag atagggttga    3540
gtgttgttcc agtttggaac aagagtccac tattaaagaa cgtggactcc aacgtcaaag    3600
ggcgaaaaac cgtctatcag ggcgatggcc cactacgtga accatcaccc taatcaagtt    3660
ttttggggtc gaggtgccgt aaagcactaa atcggaaccc taagggagc ccccgattta    3720
gagcttgacg gggaaagccg cgaacgtgg cgagaaagga agggaagaaa gcgaaaggag    3780
cgggcgctag ggcgctggca agtgtagcgg tcacgctgcg cgtaaccacc acaccgccg    3840
cgcttaatgc gccgctacag ggcgcgtccc atatggtgca ctctcagtac aatctgctct    3900
gatgccgcat agttaagcca gccccgacac ccgccaacac ccgctgacgc gccctgacgg    3960
gcttgtctgc tcccggcatc cgcttacaga caagctgtga ccgtctccgg gagctgcatg    4020
tgtcagaggt tttcaccgtc atcaccgaaa cgcgcga                              4057
```

<210> SEQ ID NO 18
<211> LENGTH: 372
<212> TYPE: DNA
<213> ORGANISM: Artificial Sequence
<220> FEATURE:
<223> OTHER INFORMATION: Synthesized DNA coding for VHH antibody

<400> SEQUENCE: 18

```
gaggtgcagc tcgtggagtc tgggggagga ttggtgcagg ctggggactc tctgagactc      60
tcctgcgcag cctctggacg taccttcatt aatcttgaca tgggctggtt ccgccagcct     120
ccagggaagg agcgtgaata cgtagcagct ataactcgaa atggtgctat aacatcgtat     180
gcggactccg cgaagggccg attcaccatc tccagagaca cgccaagaa cacggtgtct      240 ctggaaatga acagcctgaa acctgaggac acgggcgttt attactgtgc agcatattct     300
atatcgaact acggtagtgg ctggtataag cccgactact ggggccaggg ggcccaggtc     360
accgtctcct ca                                                         372
```

```
<210> SEQ ID NO 19
<211> LENGTH: 40
<212> TYPE: DNA
<213> ORGANISM: Artificial Sequence
<220> FEATURE:
<223> OTHER INFORMATION: Synthesized Primer

<400> SEQUENCE: 19
cagccggcca tggctgctga ggtgcagctc gtggagtctg                            40
```

```
<210> SEQ ID NO 20
<211> LENGTH: 37
<212> TYPE: DNA
<213> ORGANISM: Artificial Sequence
<220> FEATURE:
<223> OTHER INFORMATION: Synthesized Primer

<400> SEQUENCE: 20
atggtggcgg ccgcgtgagg agacggtgac ctgggcc                               37
```

```
<210> SEQ ID NO 21
<211> LENGTH: 405
<212> TYPE: DNA
<213> ORGANISM: Artificial Sequence
<220> FEATURE:
<223> OTHER INFORMATION: a DNA containing a gene sequence coding for the
      amino acid sequence represented by SEQ ID NO: 08

<400> SEQUENCE: 21
cagccggcca tggctgctga ggtgcagctc gtggagtctg ggggaggatt ggtgcaggct      60
ggggactctc tgagactctc ctgcgcagcc tctggacgta ccttcattaa tcttgacatg     120
ggctggttcc gccagcctcc agggaaggag cgtgaatacg tagcagctat aactcgaaat     180
ggtgctataa catcgtatgc ggactccgcg aagggccgat tcaccatctc cagagacaac     240
gccaagaaca cggtgtctct ggaaatgaac agcctgaaac tgaggacacg ggcgttttat     300
tactgtgcag catattctat atcgaactac ggtagtggct ggtataagcc cgactactgg     360
ggccaggggg cccaggtcac cgtctcctca cgcggccgcc accat                     405
```

```
<210> SEQ ID NO 22
<211> LENGTH: 33
<212> TYPE: DNA
<213> ORGANISM: Artificial Sequence
<220> FEATURE:
<223> OTHER INFORMATION: Synthesized Primer

<400> SEQUENCE: 22
cgcggccgcc accatcatca ccaccattaa tag                                   33
```

```
<210> SEQ ID NO 23
<211> LENGTH: 31
<212> TYPE: DNA
```

<213> ORGANISM: Artificial Sequence
<220> FEATURE:
<223> OTHER INFORMATION: Synthesized Primer

<400> SEQUENCE: 23
agccatggcc ggctgggccg cgagtaataa c                          31

<210> SEQ ID NO 24
<211> LENGTH: 498
<212> TYPE: PRT
<213> ORGANISM: Influenza A virus

<400> SEQUENCE: 24

```
Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asn Gly Lys Trp Met Arg Glu Leu Ile Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Val Arg Met Ile Lys Arg Gly Ile Asn Asp Arg Asn Phe Trp Arg
        195                 200                 205

Gly Glu Asn Gly Arg Lys Thr Arg Ile Ala Tyr Glu Arg Met Cys Asn
    210                 215                 220

Ile Leu Lys Gly Lys Phe Gln Thr Ala Ala Gln Lys Ala Met Met Asp
225                 230                 235                 240

Gln Val Arg Glu Ser Arg Asn Pro Gly Asn Ala Glu Phe Glu Asp Leu
                245                 250                 255

Thr Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285

Tyr Asp Phe Glu Arg Glu Gly Tyr Ser Leu Val Gly Ile Asp Pro Phe
    290                 295                 300

Arg Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335
```

```
Ala Phe Glu Asp Leu Arg Val Leu Ser Phe Ile Lys Gly Thr Lys Val
                340                 345                 350

Leu Pro Arg Gly Lys Leu Ser Thr Arg Gly Val Gln Ile Ala Ser Asn
            355                 360                 365

Glu Asn Met Glu Thr Met Glu Ser Ser Thr Leu Glu Leu Arg Ser Arg
        370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Ile Gln Pro Thr Phe Ser Val Gln Arg
                405                 410                 415

Asn Leu Pro Phe Asp Arg Thr Thr Ile Met Ala Ala Phe Asn Gly Asn
            420                 425                 430

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
    450                 455                 460

Glu Leu Ser Asp Glu Lys Ala Ala Ser Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn
```

<210> SEQ ID NO 25
<211> LENGTH: 3096
<212> TYPE: DNA
<213> ORGANISM: Artificial Sequence
<220> FEATURE:
<223> OTHER INFORMATION: a DNA obtained by amplifying a part of Vector pRA2

<400> SEQUENCE: 25

```
cgcggccgcc accatcatca ccaccattaa tagcactagt caagaggatc cggctgctaa      60
caaagcccga aggaagctg agttggctgc tgccaccgct gagcaataac tagcataacc     120
ccttggggcc tctaaacggg tcttgagggg ttttttgctg aaaggaggaa ctatatccgg    180
atgaattccg tgtattctat agtgtcacct aaatcgtatg tgtatgatac ataaggttat    240
gtattaattg tagccgcgtt ctaacgacaa tatgtacaag cctaattgtg tagcatctgg    300
cttactgaag cagaccctat catctctctc gtaaactgcc gtcagagtcg gtttggttgg    360
acgaaccttc tgagtttctg gtaacgccgt cccgcacccg gaaatggtca gcgaaccaat    420
cagcagggtc atcgctagcc agatcctcta cgccggacgc atcgtggccg gcatcaccgg    480
cgccacaggt gcggttgctg gcgcctatat cgccgacatc accgatgggg aagatcgggc    540
tcgccacttc gggctcatga gcgcttgttt cggcgtgggt atggtggcag gccccgtggc    600
cgggggactg ttgggcgcca tctccttgca tgcaccattc cttgcggcgg cggtgctcaa    660
cggcctcaac ctactactgg gctgcttcct aatgcaggag tcgcataagg gagagcgtcg    720
aatggtgcac tctcagtaca atctgctctg atgccgcata gttaagccag ccccgacacc    780
cgccaacacc cgctgacgcg ccctgacggg cttgtctgct cccggcatcc gcttacagac    840
aagctgtgac cgtctccggg agctgcatgt gtcagaggt tcaccgtca tcaccgaaac    900
gcgcgagacg aaagggcctc gtgatacgcc tatttttata ggttaatgtc atgataataa    960
tggtttctta gacgtcaggt ggcacttttc ggggaaatgt gcgcggaacc cctatttgtt   1020
tatttttcta aatacattca aatatgtatc cgctcatgag acaataaccc tgataaatgc   1080
```

-continued

```
ttcaataata ttgaaaaagg aagagtatga gtattcaaca tttccgtgtc gcccttattc      1140
ccttttttgc ggcattttgc cttcctgttt ttgctcaccc agaaacgctg gtgaaagtaa      1200
aagatgctga agatcagttg ggtgcacgag tgggttacat cgaactggat ctcaacagcg      1260
gtaagatcct tgagagtttt cgccccgaag aacgttttcc aatgatgagc acttttaaag      1320
ttctgctatg tggcgcggta ttatcccgta ttgacgccgg gcaagagcaa ctcggtcgcc      1380
gcatacacta ttctcagaat gacttggttg agtactcacc agtcacagaa aagcatctta      1440
cggatggcat gacagtaaga gaattatgca gtgctgccat aaccatgagt gataacactg      1500
cggccaactt acttctgaca acgatcggag gaccgaagga gctaaccgct ttttgcaca       1560 acatggggga tcatgtaact cgccttgatc gttgggaacc ggagctgaat gaagccatac      1620
caaacgacga gcgtgacacc acgatgcctg tagcaatggc aacaacgttg cgcaaactat      1680
taactggcga actacttact ctagcttccc ggcaacaatt aatagactgg atggaggcgg      1740
ataaagttgc aggaccactt ctgcgctcgg cccttccggc tggctggttt attgctgata      1800
aatctggagc cggtgagcgt gggtctcgcg gtatcattgc agcactgggg ccagatggta      1860
agccctcccg tatcgtagtt atctacacga cggggagtca ggcaactatg gatgaacgaa      1920
atagacagat cgctgagata ggtgcctcac tgattaagca ttggtaactg tcagaccaag      1980
tttactcata tatactttag attgatttaa aacttcattt ttaatttaaa aggatctagg      2040
tgaagatcct ttttgataat ctcatgacca aaatccctta acgtgagttt cgttccact       2100 gagcgtcaga ccccgtagaa aagatcaaag gatcttcttg agatcctttt tttctgcgcg      2160
taatctgctg cttgcaaaca aaaaaaccac cgctaccagc ggtggtttgt ttgccggatc      2220
aagagctacc aactctttt ccgaaggtaa ctggcttcag cagagcgcag ataccaaata      2280
ctgttcttct agtgtagccg tagttaggcc accacttcaa gaactctgta gcaccgccta      2340
catacctcgc tctgctaatc ctgttaccag tggctgctgc cagtggcgat aagtcgtgtc      2400
ttaccgggtt ggactcaaga cgatagttac cggataaggc gcagcggtcg gctgaacgg       2460 ggggttcgtg cacacagccc agcttggagc gaacgaccta caccgaactg agatacctac      2520
agcgtgagct atgagaaagc gccacgcttc ccgaagggag aaaggcggac aggtatccgg      2580
taagcggcag ggtcggaaca ggagagcgca cgagggagct tccaggggga aacgcctggt      2640
atctttatag tcctgtcggg tttcgccacc tctgacttga gcgtcgattt tgtgatgct       2700 cgtcagggg gcggagccta tggaaaaacg ccagcaacgc ggccttttta cggttcctgg       2760
ccttttgctg gccttttgct cacatgttct tcctgcgtt atccctgat tctgtggata       2820 accgtattac cgcctttgag tgagctgata ccgctcgccg cagccgaacg accgagcgca      2880
gcgagtcagt gagcgaggaa gcggaagagc gcccaatacg caaaccgcct ctccccgcgc      2940
gttggccgat tcattaatgc agctggctta tcgaattaa tacgactcac tataggagga      3000
cccaagcttt atttcaagga gacagtcata atgaaatacc tattgcctac ggcagccgct      3060
ggattgttat tactcgcggc ccagccggcc atggct                                3096
```

COMPOSITE COMPRISING ANTIBODY CAPABLE OF BINDING TO INTRANUCLEAR PROTEIN OF INFLUENZA VIRUS

CROSS-REFERENCE TO RELATED APPLICATIONS

This application is a Continuation of U.S. patent application Ser. No. 15/648,287, filed on Jul. 12, 2017, which is a continuation-in-part of U.S. application Ser. No. 15/296,180, filed on of Oct. 18, 2016, which in turn claims priority of Provisional Patent Application Ser. No. 62/344,152, which is filed on Jun. 1, 2016, the contents of which Applications are hereby incorporated by reference.

INCORPORATION BY REFERENCE SEQUENCE LISTING

The material contained in the ASCII text file named "P0625742US03_ST25.txt" created on May 31, 2017, and having a file size of 20,747 bytes is incorporated by reference herein.

BACKGROUND

1. Technical Field

The present invention relates to a composite comprising an antibody capable of binding to an intranuclear protein of an influenza virus. The present invention also relates to a detection device and a detection method using the composite

2. Description of the Related Art

Patent Literature 1 discloses antibodies each capable of binding to an influenza virus. At least apart of the antibodies disclosed in Patent Literature 1 are derived from an alpaca. Patent Literature 1 is incorporated herein by reference.

CITATION LIST

Patent Literature

United States Patent Application Publication No. 2014/0302063

SUMMARY

An object of the present invention is to provide a composite comprising a novel antibody capable of binding to an intranuclear protein of an influenza virus. Another object of the present invention is to provide a detection device and a detection method using the composite comprising the novel antibody.

The present invention is a composite, comprising:
an antibody; and
at least one selected from the group consisting of a solid phase support and a labeled substance,
wherein
the antibody consists of the amino acid sequence represented by SEQ ID NO: 08, and is capable of binding to an intranuclear protein of an influenza virus type A;
the influenza virus type A is at least one selected from the group consisting of H1N1, H2N2, H3N2, and H7N9; and the antibody is bound to the at least one selected from the group consisting of a solid phase support and the labeled substance.

The present invention provides a composite comprising a novel antibody capable of binding to an intranuclear protein of an influenza virus. The present invention also provides a detection device and a detection method using the composite comprising the novel antibody.

DETAILED DESCRIPTION OF THE EMBODIMENT

Figure 1A:
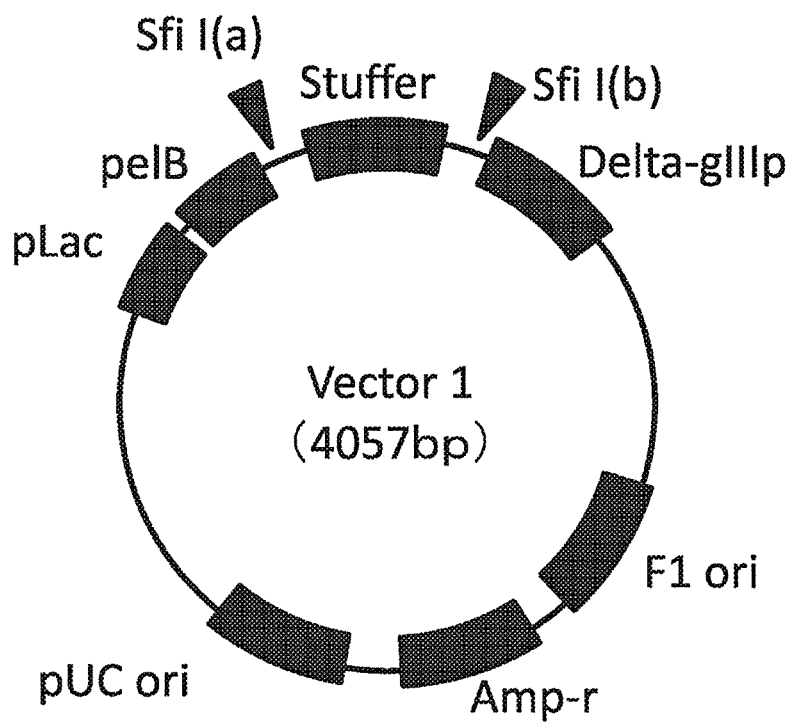
FIG. 1A is a map of a vector used to ligate various genes included in a gene library of a VHH antibody.

The antibody according to the present invention is capable of binding to an influenza virus type A. In particular, the antibody according to the present invention is capable of binding to an intranuclear protein of an influenza virus type A. As disclosed in Patent Literature 1, an antibody capable of binding to an influenza virus consists of an amino acid sequence including, in an N- to C-direction, the following structural domains.

N-FR1-CDR1-FR2-CDR2-FR3-CDR3-FR4-C wherein

FR denotes a framework region amino acid sequence and CDR denotes a complementary determining region amino acid sequence.

In the present invention, the CDR1 consists of an amino acid sequence represented by GRTFINLDMG (SEQ ID NO: 01).

In the present invention, the CDR2 consists of an amino acid sequence represented by AITRNGAITSYADSAKG (SEQ ID NO: 02).

In the present invention, the CDR3 consists of an amino acid sequence represented by YSISNYGSGWYKPDY (SEQ ID NO: 03).

Desirably, the CDR1, the CDR2, and the CDR3 are represented by SEQ ID NO: 01, SEQ ID NO: 02, and SEQ ID NO: 03, respectively. In this case, more desirably, the FR1, the FR2, the FR3, and the FR4 consist of amino acid sequences represented by EVQLVESGGGLVQAGDSL-RLSCAAS (SEQ ID NO: 04), WFRQPPGKEREYVA (SEQ ID NO: 05), RFTISRDNAKNTVSLEMNSLKPEDT-GVYYCAA (SEQ ID NO: 06), and WGQGAQVTVSS (SEQ ID NO: 07), respectively. In other words, it is more desirable that the antibody according to the present invention consists of the following amino acid sequence.

(SEQ ID NO: 08)
EVQLVESGGGLVQAGDSLRLSCAASGRTFINLDMGWFRQPPGKEREYVAA

ITRNGAITSYADSAKGRFTISRDNAKNTVSLEMNSLKPEDTGVYYCAAYS

ISNYGSGWYKPDYWMAQVTVSS

The antibody consisting of the amino acid sequence represented by SEQ ID NO: 08 does not exhibit antigen cross reactivity to an influenza virus, such as an influenza virus type B, other than the influenza virus type A.

The antibody according to the present invention is employed in a detection device or in a detection method for detecting the intranuclear protein of an influenza virus type A. In this case, the antibody according to the present invention is used in a state where the antibody is bound to at least one selected from the group consisting of a solid support and a labeled substance.

As long as the solid support is a support insoluble in a solvent used for a reaction system of an antigen-antibody reaction, a shape and a material of the solid support is not limited. An example of the shape of the solid support is a plate, a bead, a disk, a tube, a filter, and a film. An example of a material of the solid support is a polymer such as polyethylene terephthalate, cellulose acetate, polycarbonate, polystyrene, or polymethylmethacrylate, a metal such as gold, silver, or aluminum, or glass. A known method such as a physical adsorption method, a covalent binding method, an ion bonding method, or a cross-linking method is employed as a method for binding the antibody to the solid support.

For example, a labeled substance such as a fluorescent substance, a luminescent substance, a dye, and a radioactive substance is used. A known method such as a physical adsorption method, a covalent binding method, an ion bonding method, or a cross-linking method is employed as a method for binding the antibody to the labeled substance.

In the detection method in which the antibody according to the present invention is used, the composite including the antibody is brought into contact with an analyte. Then, detected is a change of a physical amount based on an antigen-antibody reaction of the intranuclear protein of the influenza virus type A contained in the analyte and the antibody included in the composite. An example of the physical amount is, for example, luminescence intensity, chromaticity, light transmission, turbidity, absorbance, or radiation dose. A known method such as an enzyme immunoassay method, an immunochromatography method, a latex agglutination method, a radioimmunoassay method, a fluorescence immunoassay method, or a surface plasmon resonance spectroscopy method is employed as an example of the detection method.

The detection device in which the antibody according to the present invention is employed includes a detector for detecting any one of the physical amount which may be changed on the basis of the antigen-antibody reaction. The detector is composed of a known device such as a photometer, a spectroscope, or a dosimeter.

EXAMPLES

Inventive Example 1

VHH antibodies (namely, heavy chain variable regions of heavy chain antibodies) capable of binding to an intranuclear protein included in an influenza virus type A H1N1 were prepared in accordance with the following procedures. Hereinafter, the intranuclear protein may be referred to as "NP".

(Immunization of Alpaca and Acquirement of Mononuclear)

In order to form a VHH antibody gene library, an alpaca was immunized using a recombinant intranuclear protein (SEQ ID NO: 24) derived from an Influenza virus type A H1N1 (A/Puerto Rico/8/34/Mount Sinai) as an antigen. The recombinant intranuclear protein was prepared using a Brevibacillus expression system by Higeta Shoyu Co., Ltd. The recombinant intranuclear protein was adjusted with an adjuvant before administrated to an alpaca.

The recombinant intranuclear protein (SEQ ID NO: 24) used in the inventive example 1 is shown below.

(SEQ ID NO: 24)
MASQGTKRSYEQMETDGERQNATEIRASVGKMIGGIGRFYIQMCTELKLS

DYEGRLIQNSLTIERMVLSAFDERRNKYLEEHPSAGKDPKKTGGPIYRRV

NGKWMRELILYDKEEIRRIWRQANNGDDATAGLTHMMIWHSNLNDATYQR

-continued

TRALVRTGMDPRMCSLMQGSTLPRRSGAAGAAVKGVGTMVMELVRMIKRG

INDRNFWRGENGRKTRIAYERMCNILKGKFQTAAQKAMMDQVRESRNPGN

AEFEDLTFLARSALILRGSVAHKSCLPACVYGPAVASGYDFEREGYSLVG

IDPFRLLQNSQVYSLIRPNENPAHKSQLVWMACHSAAFEDLRVLSFIKGT

KVLPRGKLSTRGVQIASNENMETMESSTLELRSRYWAIRTRSGGNTNQQR

ASAGQISIQPTFSVQRNLPFDRTTIMAAFNGNTEGRTSDMRTEIIRMMES

ARPEDVSFQGRGVFELSDEKAASPIVPSFDMSNEGSYFFGDNAEEYDN

Specifically, the recombinant intranuclear protein having a concentration of 100 micrograms/milliliter was administered to the alpaca. After one week, the recombinant intranuclear protein having the same concentration was administered to the alpaca, again. In this way, the alpaca was immunized with the recombinant intranuclear protein five times for five weeks. After another week, blood of the alpaca was extracted. Then, mononuclear cells were acquired from the blood as below.

A blood cell separation solution (available from COSMO BIO Co., Ltd., trade name: Lymphoprep) was added to a lymphocyte separation tube (available from Greiner Bio-One Co., Ltd., trade name: Leucosep). Then, the solution was subjected to centrifugation at a temperature of 20 degrees Celsius at 1,000×g for one minute.

The blood extracted from the alpaca was treated with heparin. Then, an equivalent amount of phosphate buffered saline (hereinafter, referred to as "PBS") was added to the thus-treated blood to obtain a sample solution. Then, the sample solution was added to the lymphocyte separation tube containing the blood cell separation solution.

The lymphocyte separation tube was subjected to centrifugation at a temperature of 20 degrees Celsius at 800×g for thirty minutes.

A fraction containing themononuclear cells was collected. PBS three times in volume was added. The fraction was subjected to centrifugation at a temperature of 20 degrees Celsius at 300×g for five minutes. The precipitate was suspended with PBS gently. After the suspending, 10 microliters of the suspension was separated in order for the count of the number of cells. The remaining suspension was subjected to centrifugation at a temperature of 20 degrees Celsius at 300×g for five minutes.

An RNA storage solution (trade name: RNA later) having a volume of 2 milliliters was added to the precipitate. Then, the solution was suspended gently. The suspension was injected into two tubes each having a volume of 1.5 milliliters. Each tube included 1 milliliter of the suspension. The tube was stored at a temperature of −20 degrees Celsius. The suspension (5 microliters) separated for the count of the number of cells was mixed with a Türk' s solution (15 microliters), and the number of the mononuclear cells was counted with a counting chamber.

(Formation of cDNA Gene Library of VHH Antibody)

Then, a total RNA was extracted from the mononuclear cells, and a cDNA gene library of VHH antibody was formed in accordance with the following procedure. In the following procedure, RNase-free-grade reagents and instruments were used.

A total RNA isolation reagent (trade name: TRIzol Regent, 1 milliliter) was added to the mononuclear cell fraction. The reagent was mixed gently with the fraction, and left at rest at room temperature for five minutes. Chloroform (200 microliters) was added to the reagent, and the reagent was shaken strongly for fifteen seconds. The reagent was left at room temperature for two-three minutes. The reagent was subjected to centrifugation at a temperature of 4 degrees Celsius at 12,000×g or less for fifteen minutes.

The supernatant was moved to a new tube. RNase-free water and chloroform (200 microliters, each) were added to the tube. In addition, 500 milliliters of isopropanol was added to the tube. The liquid included in the tube was stirred with a vortex mixer. The liquid was left at rest at room temperature for ten minutes. Then, the liquid was subjected to centrifugation at a temperature of 4 degrees Celsius at 12,000×g or less for fifteen minutes. The supernatant was removed, and the precipitate was rinsed with 1 milliliter of 75% ethanol. This solution was subjected to centrifugation at a temperature of four degrees Celsius at 7,500×g or less for five minutes. The solution was dried to obtain a total RNA. The obtained total RNA was dissolved in RNase-free water.

In order to obtain cDNA from the total RNA, a kit including a reverse transcriptase was employed. The kit was available from Takara Bio Inc., as a trade name of Prime-Script II $1^{st}$ strand cDNA Synthesis Kit. The Random 6 mer and Oligo dT primer included in the kit were used as primers. The cDNA was obtained in accordance with the standard protocol attached to the kit.

The gene of the VHH antibody included in the alpaca was obtained from the cDNA by a PCR method. An enzyme for PCR was available from Takara Bio Inc., as a trade name of Ex-taq.

The following reagents were mixed to obtain a mixture solution.

| | |
|---|---|
| 10x buffer | 5 microliters |
| dNTPs | 4 microliters |
| Primer F | 2 microliters |
| Primer R | 2 microliters |
| cDNA template | 1 microliter |
| Ex-taq | 0.25 microliters |

The mixture solution was subjected to the following PCR method.

First, the mixture solution was heated at a temperature of 95 degrees Celsius for two minutes.

Then, the temperature of the mixture solution was varied in accordance with the following cycle.

Ninety six degrees Celsius for thirty seconds,
Fifty two degrees Celsius for thirty seconds, and
Sixty eight degrees Celsius for forty seconds
This cycle was repeated thirty times.

Finally, the mixture solution was heated at a temperature of sixty eight degrees Celsius for four minutes and stored at a temperature of four degrees Celsius.

The following primers were used in the present PCR method.

Primer 1:
(SEQ ID NO: 09)
5'-GGTGGTCCTGGCTGC-3'

Primer 2:
(SEQ ID NO: 10)
5'-ctgctcctcgcGGCCCAGCCGGCCatggcTSAGKTGCAGCTCGTGGA
GTC-3'

Primer 3:
(SEQ ID NO: 11)
5'-TGGGGTCTTCGCTGTGGTGCG-3'

```
Primer 4:
                                          (SEQ ID NO: 12)
5'-TTGTGGTTTTGGTGTCTTGGG-3'

Primer 5:
                                          (SEQ ID NO: 13)
5'-tttgCtctGCGGCCGCagaGGCCgTGGGGTCTTCGCTGTGGTGCG-3'

Primer 6:
                                          (SEQ ID NO: 14)
5'-tttgCtctGCGGCCGCagaGGCCgaTTGTGGTTTTGGTGTCTTGGG-3'
```

(Reference literature: Biomed Environ Sci., 2012; 27(2): 118-121)

Three PCR assays were conducted.

In the first PCR assay, a primer set A composed of the cDNA, Primer 1 and Primer 3 and a primer set B composed of the cDNA, Primer 1 and Primer 4 were used.

In the second PCR assay, a primer set C composed of the gene amplified with the primer set A, Primer 2, and Primer 3, and a primer set D composed of the gene amplified with the primer set B, Primer 2, and Primer 4 were used.

In the third PCR assay, a primer set E composed of the gene amplified with the primer set C, Primer 2, and Primer 5, and a primer set F composed of the gene amplified with the primer set D, Primer 2, and Primer 6 were used.

In this way, the gene library of the VHH antibody was formed. In other words, the gene library of the VHH antibody included the genes amplified with the primer sets E and F.

(Formation of Phage Library)

Next, a phage library was formed from the gene library of the VHH antibody in accordance with the following procedures.

Figure 1B:
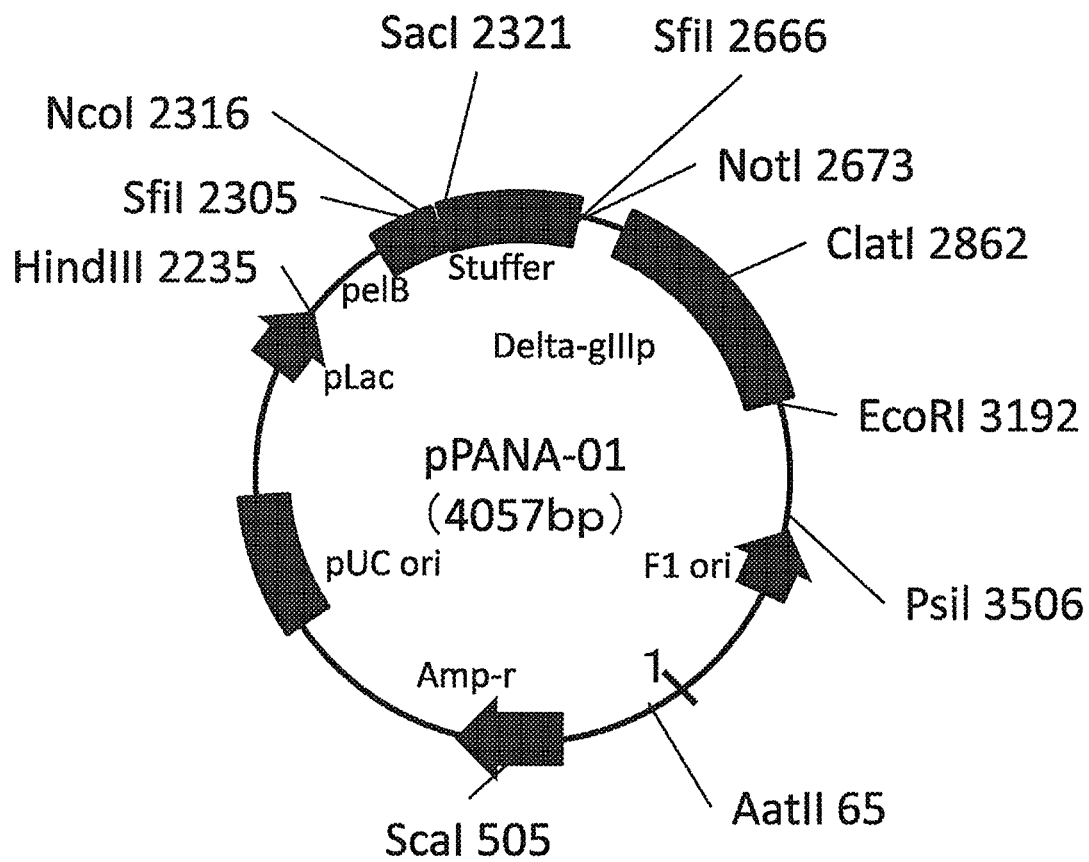
FIG. 1B shows the detail of the vector map shown in FIG. 1A.

A plasmid Vector 1 (4057 bp, see FIG. 1A) derived from a commercially available plasmid pUC119 (for example, available from Takara Bio Inc.) was treated with a restriction enzyme SfiI. The restriction enzyme site SfiI(a) shown in FIG. 1A consists of the gene sequence represented by GGCCCAGCCGGCC (SEQ ID NO: 15). The restriction enzyme site SfiI(b) consists of the gene sequence represented by GGCCTCTGCGGCC (SEQ ID NO: 16). FIG. 1B shows a detailed vector map of the plasmid Vector 1.

The plasmid Vector 1 consists of the following gene sequence.

```
                                          (SEQ ID NO: 17)
gacgaaagggcctcgtgatacgcctattttataggttaatgtcatgat aataatggtttcttagacgtcaggtggcacttttcggggaaatgtgcgc ggaacccctatttgtttattttttctaaatacattcaaatatgtatccgc tcatgagacaataaccctgataaatgcttcaataatattgaaaaaggaa gagtatgagtattcaacatttccgtgtcgcccttattccctttttttgcg gcattttgccttcctgttttttgctcacccagaaacgctggtgaaagtaa aagatgctgaagatcagttgggtgcacgagtgggttacatcgaactgga tctcaacagcggtaagatccttgagagttttcgccccgaagaacgtttt ccaatgatgagcacttttaaagttctgctatgtggcgcggtattatccc gtattgacgccgggcaagagcaactcggtcgccgcatacactattctca gaatgacttggttgagtactcaccagtcacagaaaagcatcttacggat ggcatgacagtaagagaattatgcagtgctgccataaccatgagtgata acactgcggccaacttacttctgacaacgatcggaggaccgaaggagct aaccgcttttttgcacaacatgggggatcatgtaactcgccttgatcgt tgggaaccggagctgaatgaagccataccaaacgacgagcgtgacacca cgatgcctgtagcaatggcaacaacgttgcgcaaactattaactggcga actacttactctagcttcccggcaacaattaatagactggatggaggcg gataaagttgcaggaccacttctgcgctcggcccttccggctggctggt ttattgctgataaatctggagccggtgagcgtgggtctcgcggtatcat tgcagcactggggccagatggtaagccctcccgtatcgtagttatctac acgacggggagtcaggcaactatggatgaacgaaatagacagatcgctg agataggtgcctcactgattaagcattggtaactgtcagaccaagttta ctcatatactttagattgatttaaaacttcatttttaatttaaaagg atctaggtgaagatcctttttgataatctcatgaccaaaatcccttaac gtgagttttcgttccactgagcgtcagacccccgtagaaaagatcaaagg atcttcttgagatcctttttttctgcgcgtaatctgctgcttgcaaaca aaaaaaccaccgctaccagcggtggtttgtttgccggatcaagagctac caactcttttccgaaggtaactggcttcagcagagcgcagataccaaa tactgtccttctagtgtagccgtagttaggccaccacttcaagaactct gtagcaccgcctacatacctcgctctgctaatcctgttaccagtggctg ctgccagtggcgataagtcgtgtcttaccgggttggactcaagacgata gttaccggataaggcgcagcggtcgggctgaacggggggttcgtgcaca cagcccagcttggagcgaacgacctacaccgaactgagatacctacagc gtgagctatgagaaagcgccacgcttcccgaagggagaaaggcggacag gtatccggtaagcggcagggtcggaacaggagagcgcacgagggagctt ccaggggggaaacgcctggtatctttatagtcctgtcgggtttcgccacc tctgacttgagcgtcgattttttgtgatgctcgtcagggggggcggagcct atggaaaaacgccagcaacgcggcctttttacggttcctggccttttgc tggccttttgctcacatgttctttcctgcgttatcccctgattctgtgg ataacgtattaccgcctttgagtgagctgataccgctcgccgcagccg aacgaccgagcgcagcgagtcagtgagcgaggaagcggaagagcgccca atacgcaaaccgcctctccccgcgcgttggccgattcattaatgcagct ggcacgacaggtttcccgactggaaagcgggcagtgagcgcaacgcaat taatgtgagttagctcactcattaggcacccaggctttacactttatg cttccggctcgtatgttgtgtggaattgtgagcggataacaatttcaca caggaaacagctatgaccatgattacgccAAGCTTCGAAGGAGACAGTC ATAatgaaatacctgctgccgaccgctgctgctggtctgctgctcctcg cGGCCCAGCCGGCCatggagcTCAAGATGACACAGACTACATCCTCCCT

GTCAGCCTCTCTGGGAGACAGAGTCACCATCAGTTGCAGGGCAAGTCAG

GACATTAGCGATTATTTAAACTGGTATCAGCAGAAACCAGATGGAACTG

TTAAACTCCTGATCTATTACACATCAAGTTTACACTCAGGAGTCCCATC
```

-continued
```
AAGGTTCAGTGGCGGTGGGTCTGGAACAGATTATTCTCTCACCATTAGC

AACCTGGAGCAAGAAGATATTGCCACTTACTTTTGCCAACAGGGTAATA

CGCTTCCGTGGACGTTTGGTGGAGGCACCAAGCTGGAAATCAAACGGGC

TGATGCTGCACCAACTgtaGGCCtctGCGGCCGCagaGcaaaaactcat ctcagaagaggatctgaatggggccgcaTAGggttccggtgattttgat tatgaaaagatggcaaacgctaataagggggctatgaccgaaaatgccg atgaaaacgcgctacagtctgacgctaaaggcaaacttgattctgtcgc tactgattacggtgctgctatcgatggtttcattggtgacgtttccggc cttgctaatggtaatggtgctactggtgattttgctggctctaattccc aaatggctcaagtcggtgacggtgataattcacctttaatgaataattt ccgtcaatatttaccttccctccctcaatcggttgaatgtcgcccttt gtctttagcgctggtaaaccatatgaattttctattgattgtgacaaaa taaacttattccgtggtgtctttgcgtttcttttatatgttgccaccttt tatgtatgtattttctacgtttgctaacatactgcgtaataaggagtct TAATAAgaattcactggccgtcgttttacaacgtcgtgactgggaaaac cctggcgttacccaacttaatcgccttgcagcacatcccctttcgcca gctggcgtaatagcgaagaggcccgcaccgatcgcccttcccaacagtt gcgcagcctgaatggcgaatggcgcctgatgcggtattttctccttacg catctgtgcggtatttcacaccgCATATGaAAATTGTAAgcgttaatat tttgttaaaattcgcgttaaattttgttaaatcagctcatttttaac caataggccgaaatcggcaaaatcccttataaatcaaaagaatagaccg agatagggttgagtgttgttccagtttggaacaagagtccactattaaa gaacgtggactccaacgtcaaagggcgaaaaaccgtctatcagggcgat ggcccactacgtgaaccatcaccctaatcaagttttttggggtcgaggt gccgtaaagcactaaatcggaaccctaaagggagccccgatttagagc ttgacggggaaagccggcgaacgtggcgagaaaggaagggaagaaagcg aaaggagcgggcgctagggcgctggcaagtgtagcggtcacgctgcgcg taaccaccacacccgccgcgcttaatgcgccgctacaGGGCGCGTccca tATGgtgcactctcagtacaatctgctctgatgccgcatagttaagcca gccccgacacccgccaacacccgctgacgcgccctgacgggcttgtctg ctccggcatccgcttacagacaagctgtgaccgtctccgggagctgca tgtgtcagaggttttcaccgtcatccgaaacgcgcga
```

Similarly, the gene library of the VHH antibody was treated with the restriction enzyme SfiI. In this way, VHH antibody gene fragments were obtained.

The thus-treated plasmid Vector 1 was mixed with the VHH antibody gene fragments at a ratio of 1:2. An enzyme (available from Toyobo Co. Ltd., trade name: Ligation High ver. 2) was injected into the mixture solution. The mixture solution was left at rest at a temperature of 16 degrees Celsius for two hours. In this way, each of the VHH antibody gene fragments was ligated into the plasmid Vector 1.

Coli bacteria (available from Takara Bio Inc., trade name: HST02) were transfected with the thus-ligated plasmid Vector 1.

Then, the coli bacteria were incubated for fifteen hours on a 2YT plate culture medium containing ampicillin at a concentration of 100 micrograms/milliliter. In this way, obtained was a library of phages each of which displays a protein obtained from the gene fragment included in the gene library of the VHH antibody.

After the incubation, a concentration of the library was calculated by counting the number of single colonies formed on the 2YT plate culture medium. As a result, the library of the phages had a concentration of $5 \times 10^7$/milliliter.

(Biopanning)

VHH antibodies capable of specifically binding to the intranuclear protein were obtained from the phage library in accordance with the following procedures.

In order to extract the clones each capable of binding to the antigen from among the phages which expressed the VHH antibody, biopanning was conducted twice.

Coli bacteria (HST02) into which the VHH antibody gene fragment included in the gene library of the VHH antibody was introduced were incubated at a temperature of 30 degrees Celsius in the 2YT AG culture medium containing 100 micrograms/milliliter of ampicillin and 1% glucose until a value $OD_{600}$ indicating absorbance reached 1.0. The 2YT AG culture medium has a volume of 100 milliliters. In this way, the coli bacteria were proliferated.

Helper phages (available from Invitrogen company, trade name: M13K07) were added to the coli bacteria culture medium in such a manner that the multiplicity of infection (MOI) was approximately 20.

Then, the culture medium was warmed at a temperature of 37 degrees Celsius for about thirty minutes. Then, the culture medium was subjected to centrifugation at a rotation speed of 4000 rpm for ten minutes to collect the coli bacteria. The coli bacteria were incubated overnight at a temperature of 30 degrees Celsius in a 2YTAK culture medium containing 100 micrograms/milliliter of ampicillin and 50 micrograms/milliliter of kanamycin, while subjected to centrifugation at 213 rpm. The 2YTAK culture medium has a volume of 100 milliliters.

The incubation liquid (100 milliliters) containing the thus-incubated coli bacteria was injected into two centrifugation tubes (volume: 50 milliliters, each). The two centrifugation tubes were subjected to centrifugation at a rotation speed of 4,000 rpm for ten minutes. Then, the supernatants (20 milliliters, each) were collected.

The supernatants (40 milliliters) were added to a 20% polyethylene glycol solution (10 milliliters) containing NaCl (2.5 M). Then, the mixture solution was mixed upside down. Subsequently, the mixture solution was cooled on ice for approximately one hour. The mixture solution was subjected to centrifugation at a rotation speed of 4,000 rpm for ten minutes. Then, the supernatant was removed. PBS containing 10% glycerol was injected toward the precipitate. Finally, the precipitate was loosened and dissolved. In this way, a library of phages each of which displays the VHH antibody was obtained.

(Screening of VHH Antibody Capable of Specifically Binding to NP)

(A) Immobilization of NP Antigen

NP was mixed with PBS to prepare an NP solution. The concentration of NP was 2 micrograms/milliliter. The NP solution (2 milliliters) was injected into an immunotube (available from NUNC Co., Ltd.). The NP solution was left at rest in the immunotube overnight. In this way, NP was immobilized in the immunotube.

Then, the inside of the immunotube was washed three times with PBS.

The inside of the immunotube was filled with PBS which contained 3% skim milk (available from Wako Pure Chemical Industries, Ltd.). In this way, NP was blocked as an antigen in the immunotube.

The immunotube was left at rest at room temperature for one hour. Subsequently, the inside of the immunotube was washed three times with PBS.

(B) Panning

The library of the phages each of which displays the VHH antibody (concentration: approximately 5E+11/milliliter) was mixed with 3 milliliters of PBS containing 3% skim milk to prepare a mixture solution. The mixture solution was injected into the immunotube in which the NP antigen was immobilized.

A lid formed of a parafilm was attached to the immunotube. Then, the immunotube was rotated upside down in a rotator for ten minutes.

The immunotube was left at rest at room temperature for one hour.

The inside of the immunotube was washed ten times with PBS containing 0.05% Tween 20. Hereinafter, such PBS is referred to as "PBST".

The inside of the immunotube was filled with PBST. Subsequently, the immunotube was left at rest for ten minutes. Then, the inside of the immunotube was washed ten times with PBST.

In order to extract phages each of which displays the VHH antibody bound to the NP antigen, a 100 mM trimethylamine solution (1 milliliter) was injected into the immunotube.

A lid formed of a parafilm was attached to the immunotube. Then, the immunotube was rotated upside down in a rotator for ten minutes.

In order to neutralize the solution, the solution was moved to a tube containing 1 mL of 0.5 M Tris/HCl (pH: 6.8). Again, the extraction of the phage was repeated using a 100 mM trimethylamine solution (1 milliliter). In this way, 3 mL of an extraction liquid was obtained.

The extraction liquid (1 mL) was mixed with 9 mL of coli bacteria HST02. The mixture solution was left at rest for one hour at a temperature of 30 degrees Celsius.

In order to count the number of colonies, 10 microliters of the mixture solution containing the coli bacteria HST02 was distributed onto a small plate including a 2TYA culture medium (10 milliliters/plate).

The rest of the mixture solution was subjected to centrifugation. The supernatant was removed, and the precipitate was distributed onto a large plate including a 2TYA culture medium (40 milliliters/plate). These two plates were left at rest overnight at a temperature of 30 degrees Celsius. In this way, first panning was conducted.

Second panning was conducted identically to the procedure of the first panning. In other words, the panning was repeated. In this way, the monoclonal phages on which the VHH antibody was displayed were purified.

After the second panning, a colony of the coli bacteria was picked up with a toothpick. The picked-up colony was put on one well of 96-flat-bottom plate. This was repeated. One well contained 200 microliters of a 2YTAG culture medium.

The solutions included in the wells were stirred at a rotation speed of 213 rpm at a temperature of 30 degrees Celsius.

The solution (50 microliters) containing grown coli bacteria was collected. The collected solution was mixed with 50 microliters of a 2YTA culture medium included in a plate. The 2YTA culture medium contained helper phages such that the multiplicity of infection was set to be 20. The solution was left at rest at a temperature of 37 degrees Celsius for forty minutes.

The plate including the 2YTA culture medium was subjected to centrifugation at 1,800 rpm for twenty minutes. The supernatant was removed. The precipitate contained the coli bacteria. The precipitate was mixed with 200 microliters of a 2YTAK culture medium. The mixture solution was left at rest overnight at a temperature of 30 degrees Celsius.

The mixture solution was subjected to centrifugation at 1800 rpm for twenty minutes. The supernatant containing the coli bacteria was collected.

(C) Qualitative Evaluation of Phage-Displayed VHH Antibody and Antigen by ELISA

An intranuclear protein solution having a concentration of 2 micrograms/milliliter was injected as an antigen into each of the wells of a 96-well plate (available from Thermo scientific company, trade name: maxisorp). The volume of the intranuclear protein solution in each well was 50 microliters. The 96-well plate was left at rest at room temperature for one hour. In this way, the NP antigen was immobilized in each well.

Each of the wells was washed three times with PBS. Then, PBS containing 3% skim milk (available from Wako Pure Chemical Industries, Ltd.) was injected into each well (200 microliters/well). The 96-well plate was left at rest at room temperature for one hour. In this way, the intranuclear protein was blocked in each well. Subsequently, each well was washed three times with PBS.

The monoclonal phages each of which displays the VHH antibody were injected into each well (50 microliters/well). Then, the 96-well plate was left at rest for one hour. In this way, the phages reacted with the NP antigen.

Each well was washed three times with PBST. Then, an anti-M13 antibody (available from ABCAM company, trade name; ab50370, 10,000-fold dilution) was injected into each well (50 microliters/well). Then, each well was washed three times with PBST.

A color-producing agent (available from Thermo Scientific, trade name: 1-step ultra TMB-ELISA) was injected into each well (50 microliters/well). The 96-well plate was left at rest for two minutes to cause the color-producing agent to react with the antibody.

A sulfuric acid aqueous solution (normal, i.e., 1 N) was injected into each well at a concentration of 50 microliters/well to cease the reaction.

The absorbance of the solution at a wavelength of 450 nanometers was measured.

Sixteen wells each having good absorbance measurement result were selected. The DNA sequences included in the phages contained in the selected six wells were analyzed by Greiner Company. The analysis results of the DNA sequences will be described below. The following one DNA sequence was found.

(SEQ ID NO: 18)
GAGGTGCAGCTCGTGGAGTCTGGGGGAGGATTGGTGCAGGCTGGGGACTC

TCTGAGACTCTCCTGCGCAGCCTCTGGACGTACCTTCATTAATCTTGACA

TGGGCTGGTTCCGCCAGCCTCCAGGGAAGGAGCGTGAATACGTAGCAGCT

ATAACTCGAAATGGTGCTATAACATCGTATGCGGACTCCGCGAAGGGCCG

ATTCACCATCTCCAGAGACAACGCCAAGAACACGGTGTCTCTGGAAATGA

ACAGCCTGAAACCTGAGGACACGGGCGTTTATTACTGTGCAGCATATTCT

ATATCGAACTACGGTAGTGGCTGGTATAAGCCCGACTACTGGGGCCAGGG
GGCCCAGGTCACCGTCTCCTCA

The protein synthesized from the DNA sequence represented by SEQ ID NO: 18 consists of the following amino acid sequence.

(SEQ ID NO: 08)
EVQLVESGGGLVQAGDSLRLSCAASGRTFINLDMGWFRQPPGKEREYVAA
ITRNGAITSYADSAKGRFTISRDNAKNTVSLEMNSLKPEDTGVYYCAAYS
ISNYGSGWYKPDYWMAQVTVSS (Expression of Anti-NP VHH Antibody)

Figure 2:
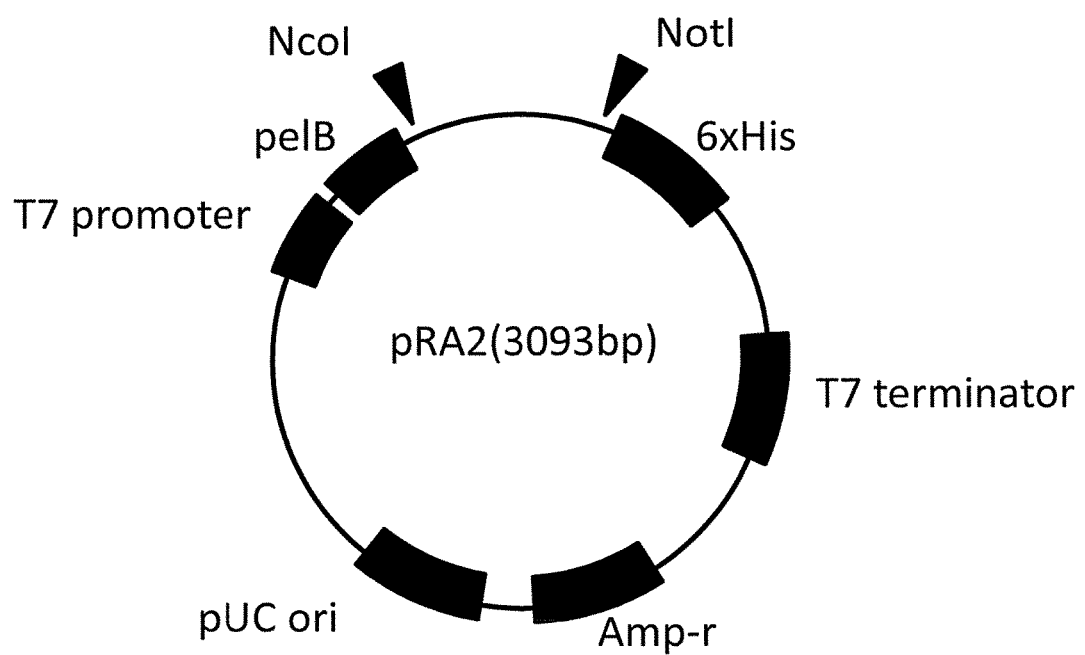
FIG. 2 is a vector map used to express the VHH antibody.
Figure 3A:
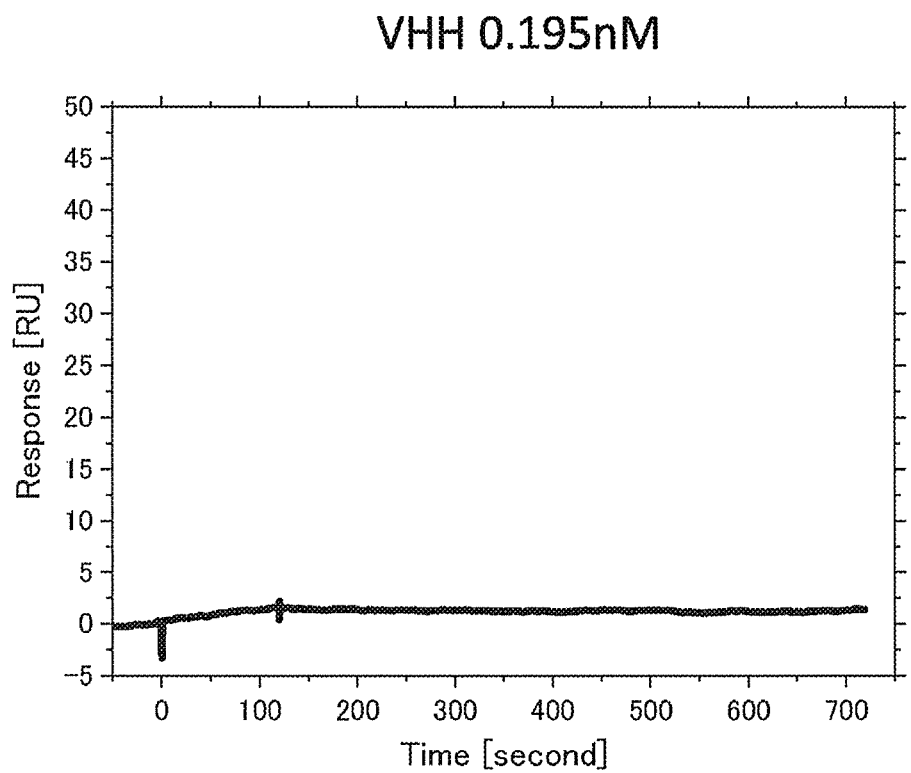
FIG. 3A is a graph showing a SPR evaluation result of the binding ability of the VHH antibody (concentration: 0.195 nM) consisting of the amino acid sequence represented by SEQ ID NO: 08 to the recombinant intranuclear protein.
Figure 3B:
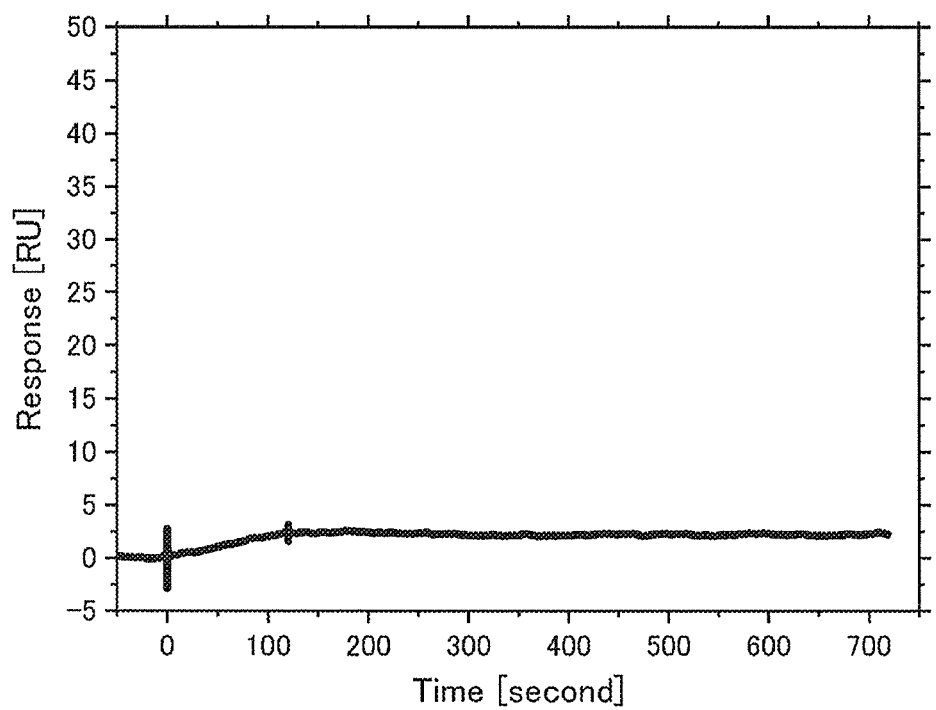
FIG. 3B is a graph showing a SPR evaluation result of the binding ability of the VHH antibody (concentration: 0.39 nM) consisting of the amino acid sequence represented by SEQ ID NO: 08 to the recombinant intranuclear protein.
Figure 3C:
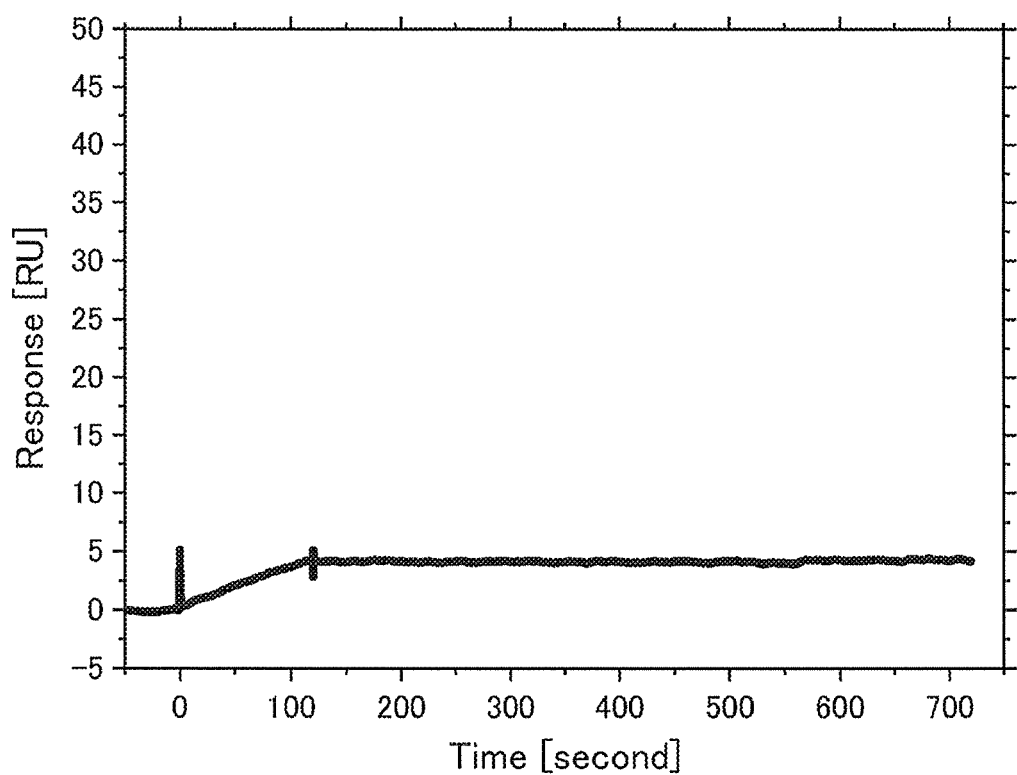
FIG. 3C is a graph showing a SPR evaluation result of the binding ability of the VHH antibody (concentration: 0.78 nM) consisting of the amino acid sequence represented by SEQ ID NO: 08 to the recombinant intranuclear protein.
Figure 3D:
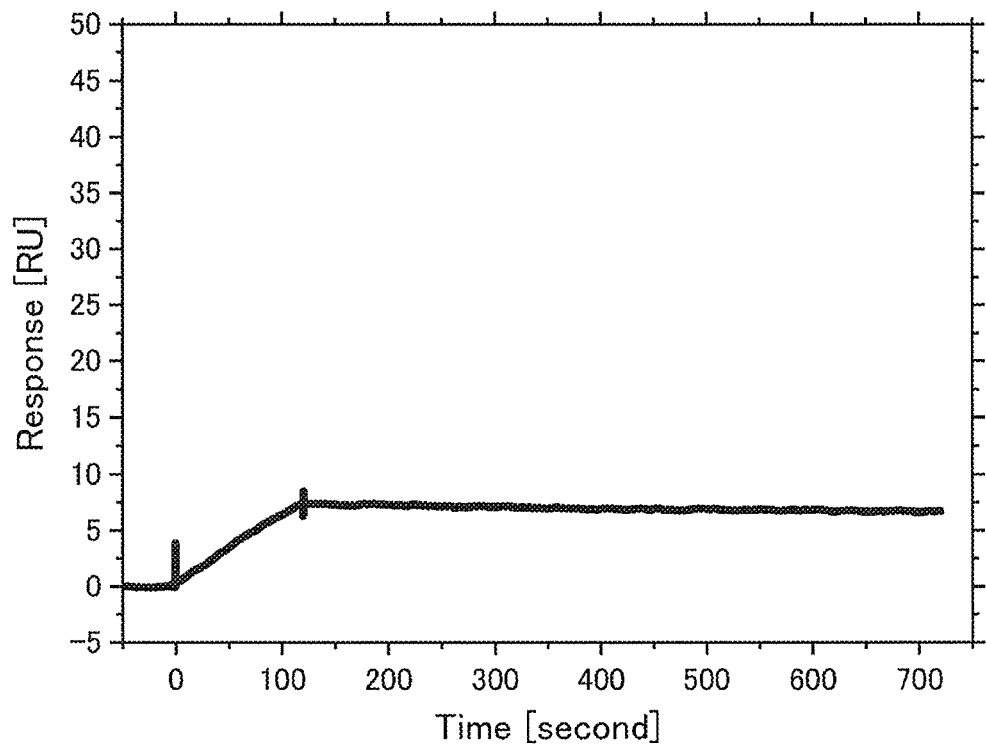
FIG. 3D is a graph showing a SPR evaluation result of the binding ability of the VHH antibody (concentration: 1.56 nM) consisting of the amino acid sequence represented by SEQ ID NO: 08 to the recombinant intranuclear protein.
Figure 3E:
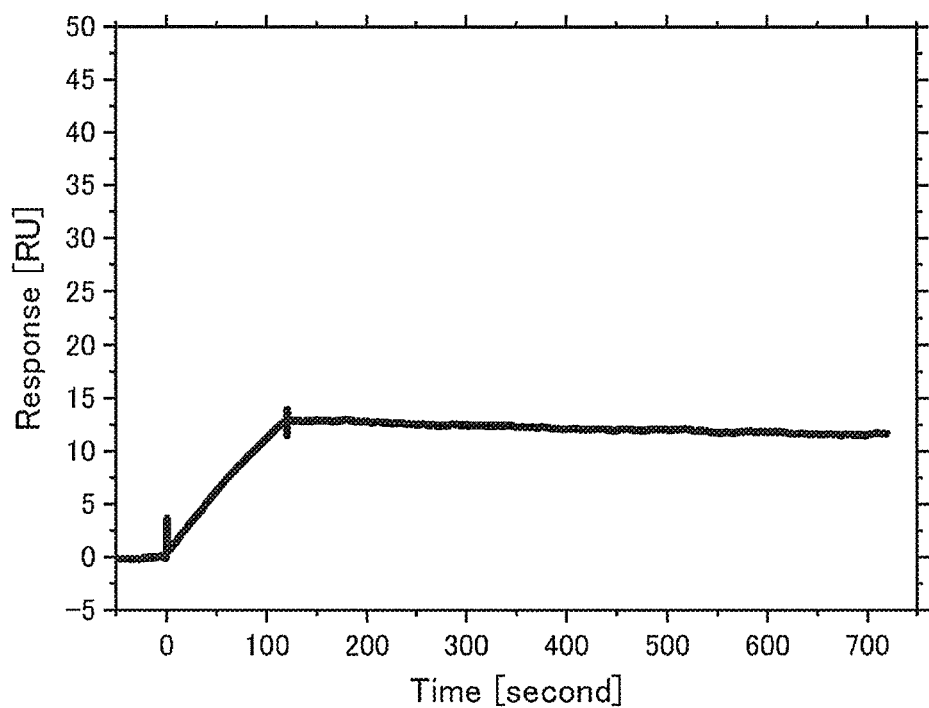
FIG. 3E is a graph showing a SPR evaluation result of the binding ability of the VHH antibody (concentration: 3.125 nM) consisting of the amino acid sequence represented by SEQ ID NO: 08 to the recombinant intranuclear protein.
Figure 3F:
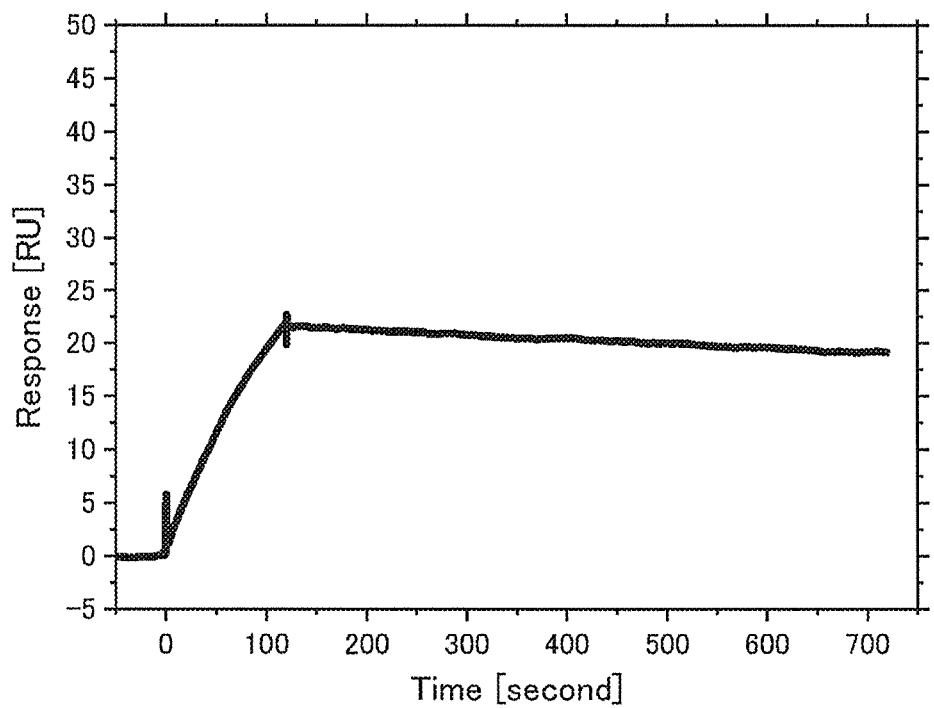
FIG. 3F is a graph showing a SPR evaluation result of the binding ability of the VHH antibody (concentration: 6.25 nM) consisting of the amino acid sequence represented by SEQ ID NO: 08 to the recombinant intranuclear protein.
Figure 3G:
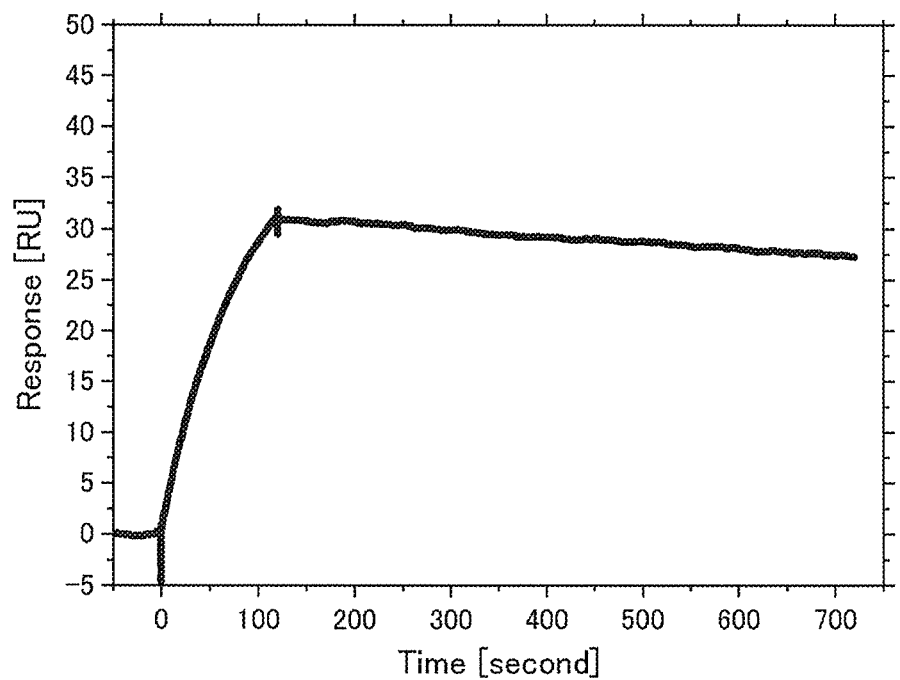
FIG. 3G is a graph showing a SPR evaluation result of the binding ability of the VHH antibody (concentration: 12.5 nM) consisting of the amino acid sequence represented by SEQ ID NO: 08 to the recombinant intranuclear protein.
Figure 3H:
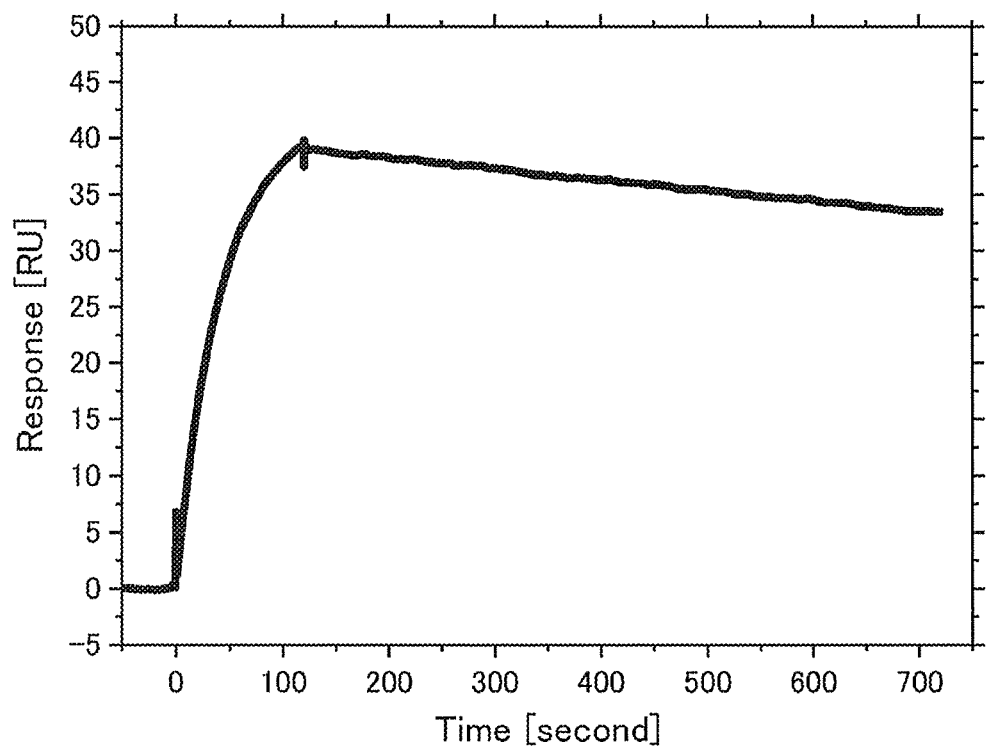
FIG. 3H is a graph showing a SPR evaluation result of the binding ability of the VHH antibody (concentration: 25 nM) consisting of the amino acid sequence represented by SEQ ID NO: 08 to the recombinant intranuclear protein.
Figure 4A:
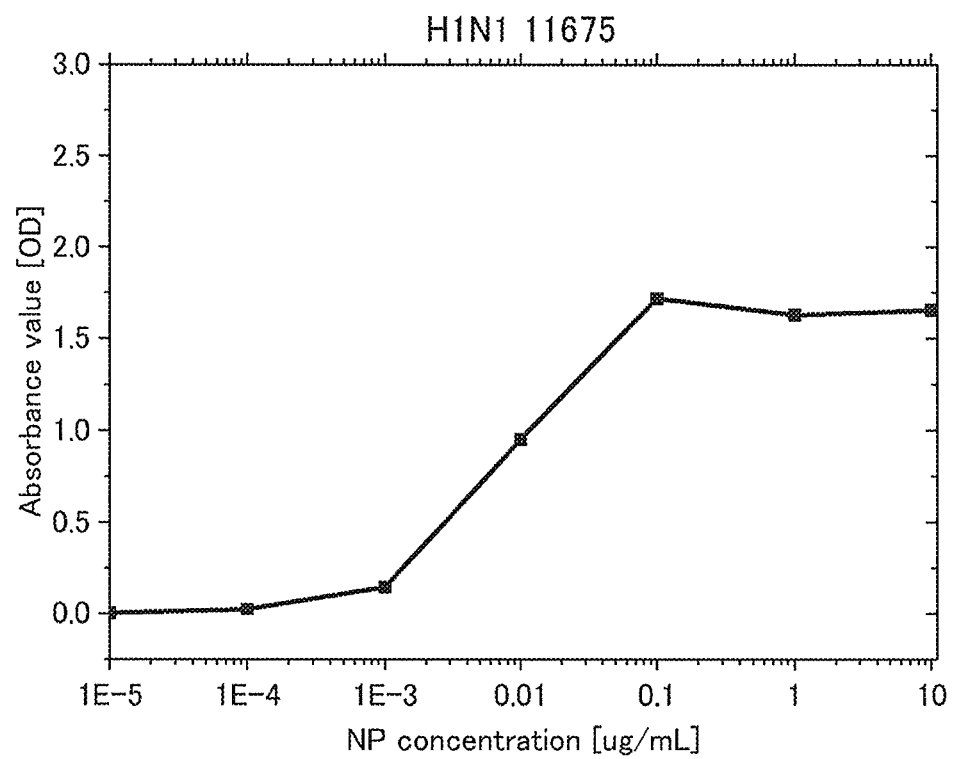
FIG. 4A is a graph showing the measurement result of the cross reactivity of the VHH antibody consisting of the amino acid sequence represented by SEQ ID NO: 08 to the influenza virus type A H1N1 11675.
Figure 4B:
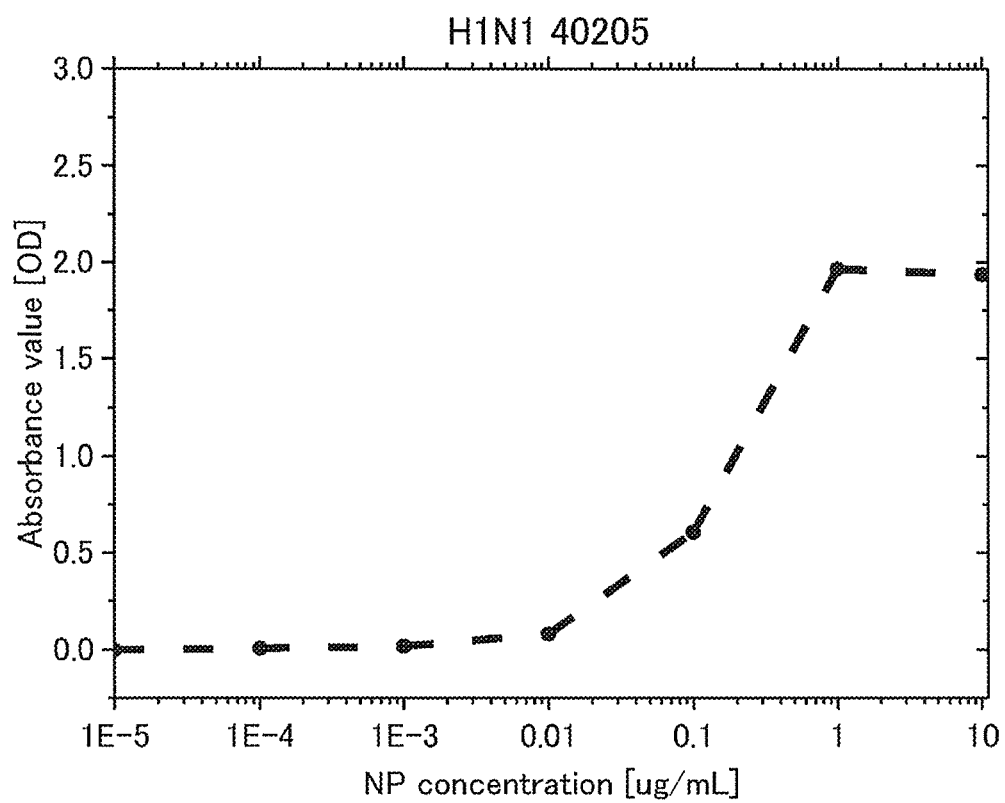
FIG. 4B is a graph showing the measurement result of the cross reactivity of the VHH antibody consisting of the amino acid sequence represented by SEQ ID NO: 08 to the influenza virus type A H1N1 40205.
Figure 4C:
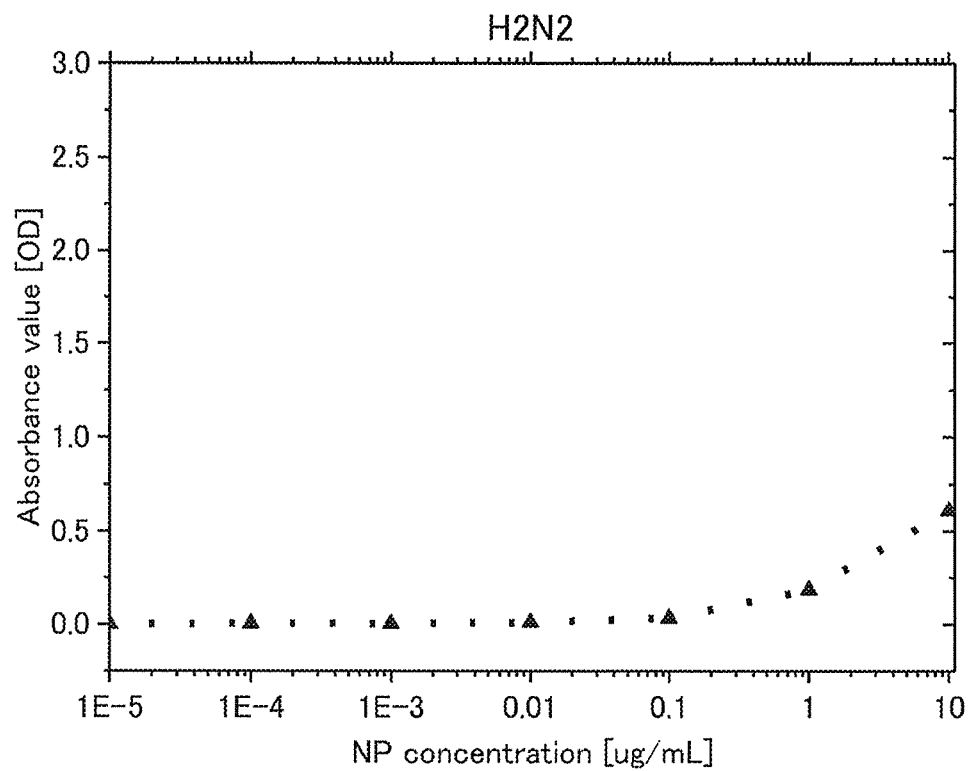
FIG. 4C is a graph showing the measurement result of the cross reactivity of the VHH antibody consisting of the amino acid sequence represented by SEQ ID NO: 08 to the influenza virus type A H2N2.
Figure 4D:
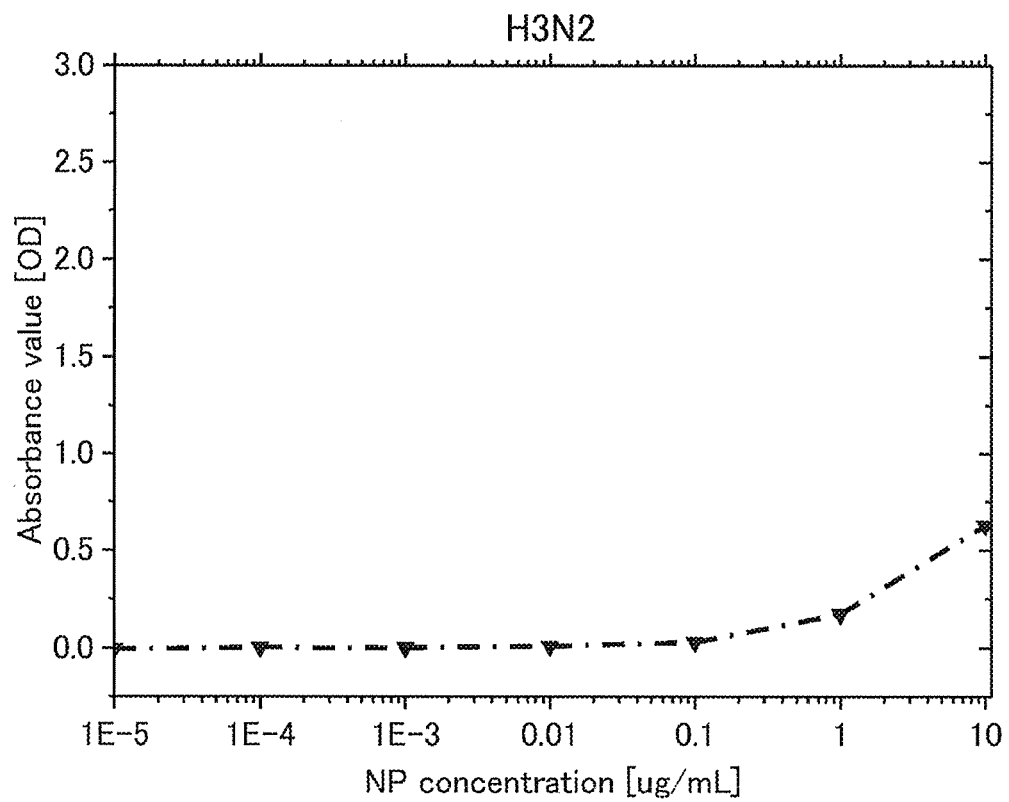
FIG. 4D is a graph showing the measurement result of the cross reactivity of the VHH antibody consisting of the amino acid sequence represented by SEQ ID NO: 08 to the influenza virus type A H3N2.
Figure 4E:
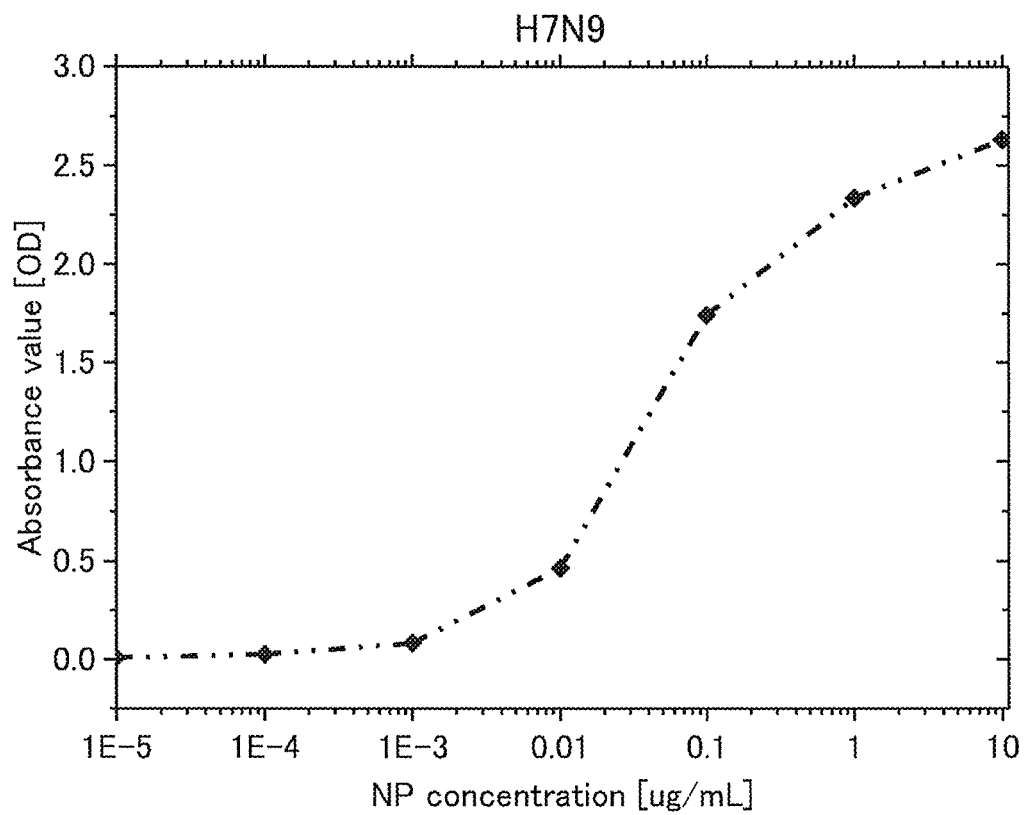
FIG. 4E is a graph showing the measurement result of the cross reactivity of the VHH antibody consisting of the amino acid sequence represented by SEQ ID NO: 08 to the influenza virus type A H7N9.
Figure 4F:
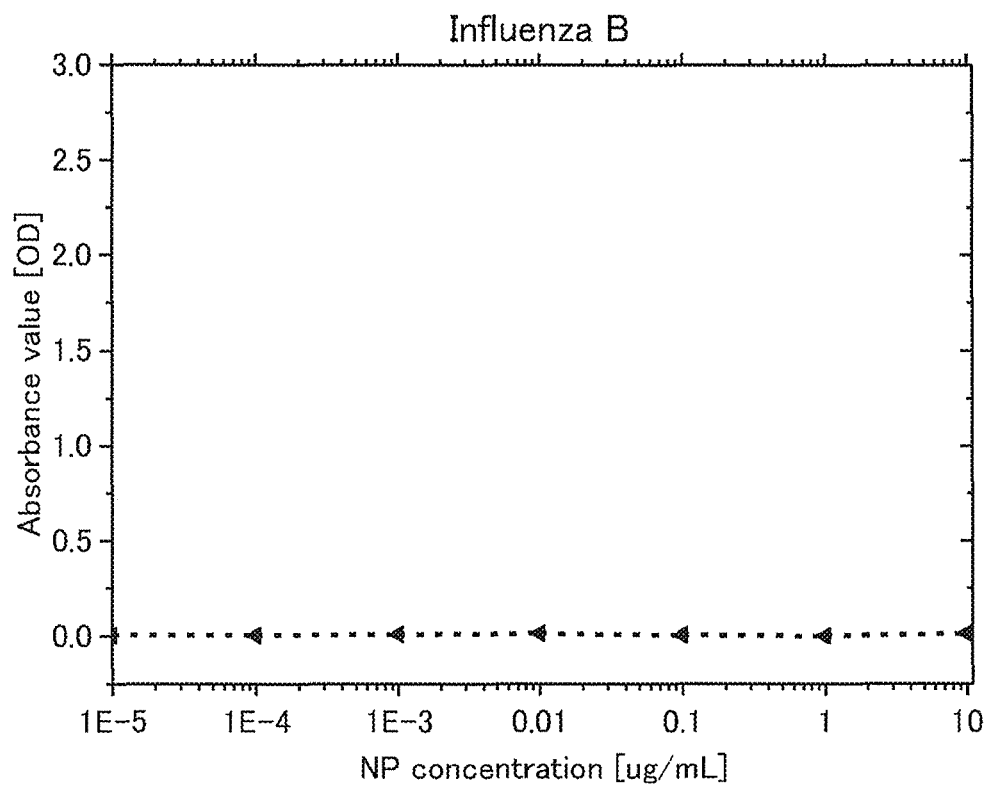
FIG. 4F is a graph showing the measurement result of the cross reactivity of the VHH antibody consisting of the amino acid sequence represented by SEQ ID NO: 08 to the influenza virus type B.

A vector pRA2(+) was purchased from Merck Millipore Company as an expression vector (see FIG. 2). Using In-Fusion HD Cloning Kit (available from Takara Bio Inc.), the VHH sequence was ligated into a vector pRA2(+). Hereinafter, the ligation process will be described in more detail.

First, a VHH antibody gene fragment was amplified by the PCR method using the following two primers (SEQ ID NO: 19 and SEQ ID NO: 20) from the plasmid Vector 1 in which the VHH antibody gene fragment included in the gene library of the VHH antibody was ligated. In this way, the following one DNA (SEQ ID NO: 21) including a gene sequence coding for the amino acid sequence represented by the SEQ ID NO: 08 was obtained.

Primer 1:
(SEQ ID NO: 19)
5'-CAGCCGGCCATGGCTGCTGAGGTGCAGCTCGTGGAGTCTG-3'

Primer 2:
(SEQ ID NO: 20)
5'-ATGGTGGCGGCCGCGTGAGGAGACGGTGACCTGGGCC-3'

(SEQ ID NO: 21)
5'-CAGCCGGCCATGGCTGCTGAGGTGCAGCTCGTGGAGTCTGGGGGAGG
ATTGGTGCAGGCTGGGGACTCTCTGAGACTCTCCTGCGCAGCCTCTGGAC
GTACCTTCATTAATCTTGACATGGGCTGGTTCCGCCAGCCTCCAGGGAAG
GAGCGTGAATACGTAGCAGCTATAACTCGAAATGGTGCTATAACATCGTA
TGCGGACTCCGCGAAGGGCCGATTCACCATCTCCAGAGACAACGCCAAGA
ACACGGTGTCTCTGGAAATGAACAGCCTGAAACCTGAGGACACGGGCGTT
TATTACTGTGCAGCATATTCTATATCGAACTACGGTAGTGGCTGGTATAA
GCCCGACTACTGGGGCCAGGGGGCCCAGGTCACCGTCTCCTCACGCGGCC
GCCACCAT-3'

On the other hand, a part of the base sequence included in the vector pRA2 was amplified by a PCR method using the following two primers (SEQ ID NO: 22 and SEQ ID NO: 23). In this way, a DNA (SEQ ID NO: 25) was obtained.

Primer 1:
(SEQ ID NO: 22)
5' CGCGGCCGCCACCATCATCACCACCATTAATAG-3'

Primer 2:
(SEQ ID NO: 23)
5'-AGCCATGGCCGGCTGGGCCGCGAGTAATAAC-3'

(SEQ ID NO: 25)
CGCGGCCGCCACCATCATCACCACCATTAATAGcactagtcaagaggatc
cggctgctaacaaagcccgaaaggaagctgagttggctgctgccaccgct
gagcaataactagcataacccttggggcctctaaacgggtcttgagggg
ttttttgctgaaaggaggaactatatccggatgaattccgtgtattctat
agtgtcacctaaatcgtatgtgtatgatacataaggttatgtattaattg
tagccgcgttctaacgacaatatgtacaagcctaattgtgtagcatctgg
cttactgaagcagaccctatcatctctcgtaaactgccgtcagagtcg
gtttggttggacgaaccttctgagtttctggtaacgccgtcccgcacccg
gaaatggtcagcgaaccaatcagcagggtcatcgctagccagatcctcta
cgccggacgcatcgtggccggcatcaccggcgccacaggtgcggttgctg
gcgcctatatcgccgacatcaccgatggggaagatcgggctcgccacttc
gggctcatgagcgcttgtttcggcgtgggtatggtggcaggcccgtggc
cggggactgttgggcgccatctccttgcatgcaccattccttgcggcgg
cggtgctcaacggcctcaacctactactgggctgcttcctaatgcaggag
tcgcataagggagagcgtcgaatggtgcactctcagtacaatctgctctg
atgccgcatagttaagccagccccgacacccgccaacacccgctgacgcg
ccctgacgggcttgtctgctcccggcatccgcttacagacaagctgtgac
cgtctccgggagctgcatgtgtcagaggttttcaccgtcatcaccgaaac
gcgcgagacgaaagggcctcgtgatacgcctattttataggttaatgtc
atgataataatggtttcttagacgtcaggtggcacttttcggggaaatgt
gcgcggaacccctatttgtttattttctaaatacattcaaatatgtatc
cgctcatgagacaataaccctgataaatgcttcaataatattgaaaaagg
aagagtatgagtattcaacatttccgtgtcgcccttattccctttttgc
ggcattttgccttcctgttttgctcacccagaaacgctggtgaaagtaa
aagatgctgaagatcagttgggtgcacgagtgggttacatcgaactggat
ctcaacagcggtaagatccttgagagttttcgccccgaagaacgttttcc
aatgatgagcacttttaaagttctgctatgtggcgcggtattatcccgta
ttgacgccgggcaagagcaactcggtcgccgcatacactattctcagaat
gacttggttgagtactcaccagtcacagaaaagcatcttacggatggcat
gacagtaagagaattatgcagtgctgccataaccatgagtgataacactg
cggccaacttacttctgacaacgatcggaggaccgaaggagctaaccgct
tttttgcacaacatgggggatcatgtaactcgccttgatcgttgggaacc
ggagctgaatgaagccataccaaacgacgagcgtgacaccacgatgcctg
tagcaatggcaacaacgttgcgcaaactattaactggcgaactacttact
ctagcttcccggcaacaattaatagactggatggaggcggataaagttgc
aggaccacttctgcgctcggcccttccggctggctggtttattgctgata
aatctggagccggtgagcgtgggtctcgcggtatcattgcagcactgggg
ccagatggtaagccctcccgtatcgtagttatctacacgacggggagtca
ggcaactatggatgaacgaaatagacagatcgctgagataggtgcctcac
tgattaagcattggtaactgtcagaccaagtttactcatatatactttag -continued

```
attgatttaaaacttcattttttaatttaaaaggatctaggtgaagatcct ttttgataatctcatgaccaaaatcccttaacgtgagttttcgttccact gagcgtcagacccgtagaaaagatcaaaggatcttcttgagatcctttt tttctgcgcgtaatctgctgcttgcaaacaaaaaaaccaccgctaccagc ggtggtttgtttgccggatcaagagctaccaactcttttttccgaaggtaa ctggcttcagcgagcgcagataccaaatactgttcttctagtgtagccgt agttaggccaccacttcaagaactctgtagcaccgcctacatacctcgct ctgctaatcctgttaccagtggctgctgccagtggcgataagtcgtgtct taccgggttggactcaagacgatagttaccggataaggcgcagcggtcgg gctgaacggggggttcgtgcacacagcccagcttggagcgaacgacctac accgaactgagatacctacagcgtgagctatgagaaagcgccacgcttcc cgaagggagaaaggcggacaggtatccggtaagcggcagggtcggaacag gagagcgcacgagggagcttccaggggggaaacgcctggtatctttatagt cctgtcgggtttcgccacctctgacttgagcgtcgattttttgtgatgctc gtcagggggcggagcctatggaaaaacgccagcaacgcggccttttttac ggttcctggccttttgctggccttttgctcacatgttctttcctgcgtta tccctgattctgtggataaccgtattaccgcctttgagtgagctgatac cgctcgccgcagccgaacgaccgagcgcagcgagtcagtgagcgaggaag cggaagagcgcccaatacgcaaaccgcctctccccgcgcgttggccgatt cattaatgcagctggcttatcgaaattaatacgactcactatagggagac ccaagctttatttcaaggagacagtcataATGaaatacctattgcctacg gcagccgctggattgttattactcgcggcccagccggccatggct
```

DNAs other than the following two DNAs (I) and (II) were fragmented with a restriction enzyme DpnI (available from TOYOBO). In other words, the following two DNAs (I) and (II) remained unchanged; however, the rest of the DNAs were fragmented.

(I) the DNA represented by SEQ ID NO: 21, and
(II) the DNA represented by SEQ ID NO: 25.

The DNA represented by SEQ ID NO: 21 was fused with the DNA represented by the SEQ ID NO: 25 using In-Fusion HD Cloning Kit (available from Takara Bio Inc.). In this way, the VHH antibody gene fragment was ligated into the vector pRA2(+).

The ligation solution (10 microliters) and coli bacteria JM109 (available from Takara Bio, 100 microliters) were mixed on ice. The mixture solution was left at rest on the ice for thirty minutes. Then, the mixture solution was heated at a temperature of 42 degrees Celsius for forty five seconds. Finally, the mixture solution was left at rest on the ice for three minutes. This procedure is known as a general heat shock method.

After the incubation at a temperature of 37 degrees Celsius for one hour with shaking, the total amount of the mixture solution was distributed onto an LBA culture medium containing ampicillin at a concentration of 100 micrograms/milliliter. The LBA culture medium was left at rest overnight at a temperature of 37 degrees Celsius.

Three colonies were selected from among the colonies formed on the LBA culture medium. The selected three colonies were incubated overnight in the LBA culture medium (3 milliliters).

The plasmids contained in the incubated coli bacteria were extracted from the LBA culture medium using a plasmid extraction kit (available from Sigma, trade name: Gene Elute Plasmid Mini Kit). In order to confirm that the gene of the targeted VHH antibody was inserted in the plasmid, the sequence of the plasmid was analyzed by Greiner Company. For the analysis of the sequence, a general T7 promotor primer set was used.

Selected were plasmids which were confirmed through the analysis of the sequence to have been formed as planned.

Coli bacteria (Competent Cell BL21 (DE3) pLysS, available from Life Technologies Company) were transfected with the selected plasmids by a heat shock method.

An LBA culture medium (1 milliliter) was injected into the solution containing the transfected coli bacteria. Then, the coli bacteria were rescued at a temperature of 37 degrees Celsius for one hour, while shaken at 213 rpm.

Then, the coli bacteria solution was collected. The collected coli bacteria solution (1 milliliter) was distributed onto an LBA culture medium. The LBA culture medium was left at rest overnight at a temperature of 37 degrees Celsius.

One colony was selected from among the colonies formed in the LBA culture medium. The selected colony was picked up with a toothpick. The picked-up colony was incubated in an LBA culture medium (3 milliliters) at a temperature of 37 degrees Celsius, while shaken at 213 rpm. In this way, a culture liquid was obtained.

In addition, the culture liquid (3 milliliters) was mixed with an LBA culture medium (1,000 milliliters). Until the absorbance of the mixture solution at a wavelength of 600 nanometers reached 0.6, the mixture solution was shaken at 120 rpm at a temperature of 28 degrees Celsius.

After the absorbance reached 0.6, an isopropylthiogalactoside solution (hereinafter, referred to as "IPTG solution") was added to the mixture solution. The final concentration of the IPTG solution was 0.5 mM. The coli bacteria contained in the mixture solution were incubated at a temperature of 20 degrees Celsius overnight. In order to collect the thus-incubated coli bacteria, the mixture solution was subjected to centrifugation at 6,000 rpm at a temperature of 4 degrees Celsius for ten minutes.

The collected coli bacteria were mixed with a mixture solvent containing 50 mM Tris-HCl, 500 mM NaCl, and 5 mM imidazole. The mixture solvent had a volume of 50 milliliters. The coli bacteria contained in the mixture solution were disintegrated with an ultrasonic wave.

The disintegration liquid containing coli bacteria was subjected to centrifugation at 40,000 g at a temperature of 4 degrees Celsius for thirty minutes to obtain an eluate. The supernatant was collected. The collected supernatant was filtered through a 0.45-micrometer filter.

The filtrate was purified with Ni-NTA-Agarose (available from QIAGEN) in accordance with recommended protocol. For the purification, an elution buffer having a total amount of 3 milliliters was used for 1 milliliter of Ni-NTA-Agarose.

Furthermore, the eluate containing the anti-NP antibody was purified with a column chromatograph (available from General Electric Company, trade name: Akita purifier). In this way, a solution containing the anti-NP antibody was obtained.

The anti-NP antibody contained in the thus-obtained solution was quantified with an absorption spectrometer (available from Scrum Inc., trade name: nanodrop) on the basis of the absorption measurement value at a wavelength of 280 nanometers. As a result, the concentration of the anti-NP antibody was 2.32 milligrams/milliliter.

(D-1) Surface Plasmon Resonance Evaluation of Anti-NP Antibody Using Recombinant NP The anti-NP antibody was evaluated as below with a recombinant NP and a surface plasmon resonance evaluation device. The details of the surface plasmon resonance (hereinafter, referred to as "SPR") will be described below.

SPR evaluation device: T200 (available from GE Healthcare)

Immobilization buffer: PBST containing 0.05% of Tween 20

Running buffer: PBST containing 0.05% of Tween 20

Sensor chip: CM5 (available from GE Healthcare)

Immobilization reagents: N-hydroxysuccinimide (NHS) and N-[3-(Dimethylamino)propyl]-N'-ethylcarbodiimide (EDC)

Anti-Flag antibody: Monoclonal ANTI-FLAG antibody (available from SIGMA)

NP: recombinant nucleoprotein (NP) protein derived from influenza virus H1N1 to which a Flag tag was fused and which was prepared using baculovirus The anti-Flag antibody was immobilized in accordance with the wizard included in the control software of the SPR evaluation device T200. For the immobilization of the anti-Flag antibody, an acetic acid solution having a pH of 5.0 was used.

The anti-NP antibody consisting of the amino acid sequence represented by SEQ ID NO: 08 was used as an analyte. In the first to eight analyses, the concentrations of the anti-NP antibody contained in the running buffer were adjusted to 0.195 nM, 0.39 nM, 0.78 nM, 1.56 nM, 3.125 nM, 6.25 nM, 12.5 nM, and 25 nM, respectively. First, the recombinant intranuclear proteins were captured with the anti-Flag antibodies. Then, the anti-NP antibodies were supplied. In this way, the anti-NP antibodies were evaluated. FIGS. 3A-3H are graphs showing an evaluation result outputted from the SPR evaluation device T200. The dissociation constant Kd was calculated using the evaluation software (available from GE Healthcare). As a result, the dissociation constant Kd was 0.224 nM.

(D-2) Evaluation of Cross Reactivity to Other Influenza Virus Subtypes by ELISA

Next, in order to evaluate binding ability of the VHH antibody consisting of the amino acid sequence represented by SEQ ID NO: 08 to recombinant nucleoproteins (namely, NPs) derived from influenza subtype viruses type A H2N2, H3N2, and H7N9, the binding ability to the recombinant intranuclear proteins was evaluated by an ELISA measurement method.

A solution containing a recombinant nucleoprotein derived from influenza virus subtype A H1N1 (available from Sino Biological Company, trade name: 11675-V08H) at a concentration of 500 micrograms/milliliter was prepared.

Similarly, four solutions containing recombinant nucleoproteins derived from influenza virus subtypes A H1N1, H2N2, H3N2, and H7N9 (available from Sino Biological Company, trade name: 40205-V08H, 40033-V08H, 40208-V08H, and 40111-V08H) at a concentration of 500 micrograms/milliliter, respectively, were prepared.

Furthermore, a solution containing a recombinant nucleoprotein (available from ORLA) derived from influenza virus subtype B at a concentration of 500 micrograms/milliliter was prepared. Hereinafter, the six solutions are referred to as "solution group A"

A part of each of the six solutions included in the solution group A was diluted 50-fold with PBST containing both of 5% skim milk (available from Wako Pure Chemical Industries Ltd.) and 0.05% Tween 20 (hereinafter, this PBST is referred to as "skim-milk-containing PBST"). In this way, a diluted solution group B (concentration: 10 micrograms/milliliter) including six diluted solutions of the recombinant NPs was obtained.

A part of each of the six solutions included in the diluted solution group B was diluted 10-fold again with the skim-milk-containing PBST. In this way, a diluted solution group C (concentration: 1 microgram/milliliter) including six diluted solutions of the recombinant NPs was obtained. This was repeated to obtain a diluted solution group D (concentration: 0.1 microgram/milliliter), a diluted solution group E (concentration: 0.01 microgram/milliliter), a diluted solution group F (concentration: 0.001 microgram/milliliter), a diluted solution group G (concentration: $1 \times 10^{-4}$ microgram/milliliter), and a diluted solution group H (concentration: $1 \times 10^{-5}$ microgram/milliliter).

The solution containing the VHH antibody consisting of the amino acid sequence represented by SEQ ID NO: 08 (concentration: 5 micrograms/milliliter) was injected into the wells of 96-well plate (Maxisorp, Nunc). Each of the wells contained 200 microliters of the solution. The 96-well plate was left at rest at room temperature for two hours to immobilize the virus in the wells.

The skim-milk-containing PBST was injected into each well to block the virus. The volume of the PBST injected into each well was 250 microliters. The 96-well plate was left at rest at room temperature for three hours.

PBST containing 0.05% Tween 20 was injected into each well to wash the wells. The PBST had a pH of 7.4. The volume of the PBST injected into each well was 200 microliters. This was repeated twice.

Each of the diluted solutions of the recombinant NPs included in the diluted solution groups B-H was injected into each well. As a reference, the skim-milk-containing PBST was injected into another well. This well including the skim-milk-containing PBST only was used as a reference to remove a background in measurement. The volume of the solutions injected into each well was 100 microliters. The 96-well plate was left at rest at room temperature. In this way, the recombinant NPs contained in the diluted solutions included in the diluted solution groups B-H were bound to the anti-NP VHH antibodies contained in the wells. The 96-well plate was left at rest at room temperature for one hour.

PBST containing 0.05% Tween 20 was injected into each well to wash the wells. The PBST had a pH of 7.4. The volume of the PBST injected into each well was 200 microliters. This was repeated five times.

The anti-NP antibody (available from abcam company, trade name: ab110661) was diluted with the PBST containing 0.05% Tween 20 (concentration: 5 micrograms/milliliter), and injected into each well. The volume of the PBST injected into each well was 100 microliters. In this way, the anti-NP antibody was bound to the recombinant NPs contained in the wells. The 96-well plate was left at rest at room temperature for one hour.

PBST containing 0.05% Tween 20 was injected into each well to wash the wells. The PBST had a pH of 7.4. The volume of the PBST injected into each well was 200 microliters. This was repeated five times.

Labelled antibodies (available from Santa Cruz company, trade name: goat anti-mouse IgG-HRP) were diluted 20,000-fold with PBST containing 0.05% Tween 20. The thus-diluted labelled antibodies were injected into each well (50 microliters/well). Then, the 96-well plate was left at rest for one hour.

PBST containing 0.05% Tween 20 was injected into each well to wash the wells. The PBST had a pH of 7.4. The volume of the PBST injected into each well was 200 microliters. This was repeated five times.

The color-producing agent (available from Thermo Scientific, trade name: 1-step ultra TMB-ELISA) was injected into each well (50 microliters/well). The 96-well plate was left at rest for thirty minutes to cause the color-producing agent to react with the antibody.

A color-stopping agent (avail able from ScyTek laboratories, trade name: TMB Stop Buffer) containing sulfuric acid and hydrochloric acid at a low concentration was injected into each well at a concentration of 50 microliters/well to cease the reaction.

The absorbance of the solution at a wavelength of 450 nanometers was measured. FIGS. 4A-4F are graphs showing the measurement result of the cross reactivity of the VHH antibody consisting of the amino acid sequence represented by SEQ ID NO: 08 to the influenza virus type A H1N1 11675, H1N1 40205, H2N2, H3N2, H7N9, and the influenza virus type B, respectively.

As understood from FIGS. 4A-4F, the VHH antibody consisting of the amino acid sequence represented by SEQ ID NO: 08 has high cross reactivity to the recombinant intranuclear proteins derived from influenza viruses type A H1N1, H2N2, H3N2, and H7N9. On the other hand, the VHH antibody consisting of the amino acid sequence represented by SEQ ID NO: 08 has low cross reactivity to the influenza virus type B.

INDUSTRIAL APPLICABILITY

The present invention provides a composite comprising a novel antibody capable of binding to the intranuclear protein of the influenza virus. The present invention also provides a detection device and a detection method using the composite comprising the novel antibody.

The invention claimed is:

1. An antibody that consists of an amino acid sequence, wherein said amino acid sequence consists of, in an N- to C-direction, the following structural domains:

N-FR1-CDR1-FR2-CDR2-FR3-CDR3-FR4-C wherein
   FR denotes a framework region amino acid sequence and CDR denotes a complementary determining region amino acid sequence;
   the CDR1 consists of an amino acid sequence represented by GRTFINLDMG (SEQ ID NO: 01);
   the CDR2 consists of an amino acid sequence represented by AITRNGAITSYADSAKG (SEQ ID NO: 02);
   the CDR3 consists of an amino acid sequence represented by YSISNYGSGWYKPDY (SEQ ID NO: 03);
   the antibody is capable of binding to an influenza virus type A;
   the influenza virus type A is at least one kind selected from the group consisting of H1N1, H2N2, H3N2, and H7N9; and
   the FR1, the FR2, the FR3, and the FR4 consist of amino acid sequences represented by EVQLVESGGGLVQAGDSLRLSCAAS (SEQ ID NO: 04), WFRQPPGKEREYVA (SEQ ID NO: 05), RFTISRDNAKNTVSLEMNSLKPEDTGVYYCAA (SEQ ID NO: 06), and WGQGAQVTVSS (SEQ ID NO: 07), respectively.

2. A bead, comprising:
   an antibody,
   wherein
   the antibody is bound to a surface of the bead; and
   the antibody that consists of an amino acid sequence, wherein said amino acid sequence consists of, in an N- to C-direction, the following structural domains:

N-FR1-CDR1-FR2-CDR2-FR3-CDR3-FR4-C wherein
   FR denotes a framework region amino acid sequence and CDR denotes a complementary determining region amino acid sequence;
   the CDR1 consists of an amino acid sequence represented by GRTFINLDMG (SEQ ID NO: 01);
   the CDR2 consists of an amino acid sequence represented by AITRNGAITSYADSAKG (SEQ ID NO: 02);
   the CDR3 consists of an amino acid sequence represented by YSISNYGSGWYKPDY (SEQ ID NO: 03);
   the antibody is capable of binding to an influenza virus type A;
   the influenza virus type A is at least one kind selected from the group consisting of H1N1, H2N2, H3N2, and H7N9; and
   the FR1, the FR2, the FR3, and the FR4 consist of amino acid sequences represented by EVQLVESGGGLVQAGDSLRLSCAAS (SEQ ID NO: 04), WFRQPPGKEREYVA (SEQ ID NO: 05), RFTISRDNAKNTVSLEMNSLKPEDTGVYYCAA (SEQ ID NO: 06), and WGQGAQVTVSS (SEQ ID NO: 07), respectively.

3. A bead, comprising:
   an antibody,
   wherein
   the antibody is bound to a surface of the bead; and
   the antibody consists of the amino acid sequence represented by SEQ ID NO: 08.

4. An antibody consisting of the amino acid sequence represented by SEQ ID NO: 08.

* * * * *